United States Patent [19]
Firica et al.

[11] Patent Number: 5,013,314
[45] Date of Patent: May 7, 1991

[54] INSTRUMENTATION AND METHOD FOR INSERTING FLEXIBLE IMPLANTS INTO FRACTURED BONES

[75] Inventors: Andrei Firica; Alexandru I. B. Manof; Dragos Gheorghiu, all of Bucharest, Romania

[73] Assignee: Intreprinderea Industria Tehnico-Medicala, Bucharest, Romania

[21] Appl. No.: 359,837

[22] Filed: May 31, 1989

Related U.S. Application Data

[63] Continuation-in-part of Ser. No. 97,968, filed as PCT RO86/00001 on Sep. 18, 1986, abandoned.

[30] Foreign Application Priority Data

Nov. 5, 1985 [RO] Romania .................. 120633

[51] Int. Cl.$^5$ .................................. A61F 5/04
[52] U.S. Cl. ........................ 606/64; 606/67; 606/72; 606/80; 606/84; 606/86; 606/96; 606/104
[58] Field of Search ............ 606/53, 64, 65, 66, 606/67, 72, 80, 84, 86, 96, 104

[56] References Cited

U.S. PATENT DOCUMENTS

| 4,135,507 | 1/1979 | Harris | 606/64 |
| 4,381,770 | 5/1983 | Neufeld | 606/96 |
| 4,473,069 | 9/1984 | Kolmert | 606/64 |
| 4,483,335 | 11/1984 | Tornier | 606/64 |
| 4,503,847 | 3/1985 | Mouradian | 606/64 |
| 4,712,541 | 12/1987 | Harder | 606/67 |
| 4,823,780 | 4/1989 | Odensten | 606/96 |
| 4,915,092 | 4/1990 | Firicá | 606/64 |

FOREIGN PATENT DOCUMENTS

| 0735251 | 6/1980 | U.S.S.R. | 606/84 |
| 1253630 | 8/1986 | U.S.S.R. | 606/80 |

Primary Examiner—Robert A. Hafer
Assistant Examiner—Michael Brown
Attorney, Agent, or Firm—Herbert Dubno

[57] ABSTRACT

An instrument set is provided for driving flexible bone implants into fractured long bones and then extracting them after the bones have mended, the set having a plurality of tools adapted to be held individually and interchangeably in a multi-functional handle, with specific tools being used to insert specific implants choosen according to the type and location of the fracture.

9 Claims, 11 Drawing Sheets

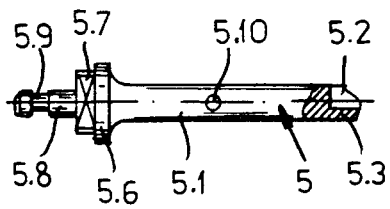
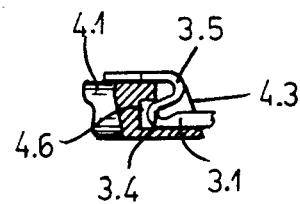
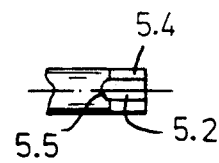
FIG.13　　　　　FIG.12　　　　　FIG.14
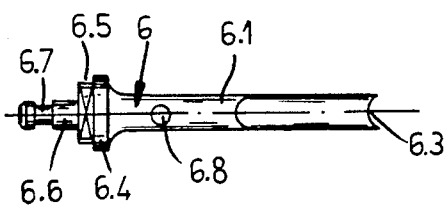
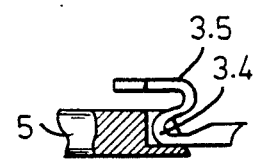
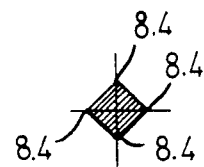
FIG.16　　　　　FIG.15　　　　　FIG.21
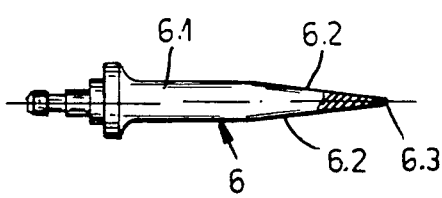
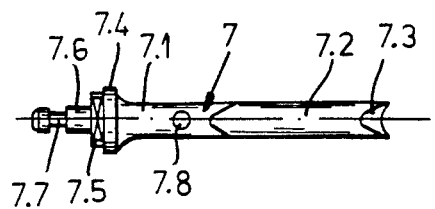
FIG.17　　　　　　　　　FIG.18
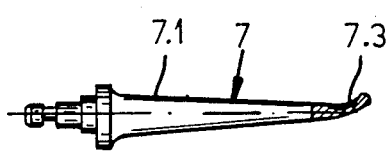
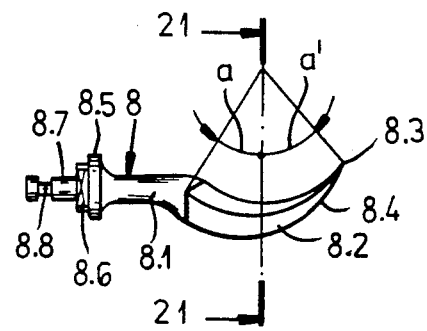
FIG.19　　　　　　　　　FIG.20

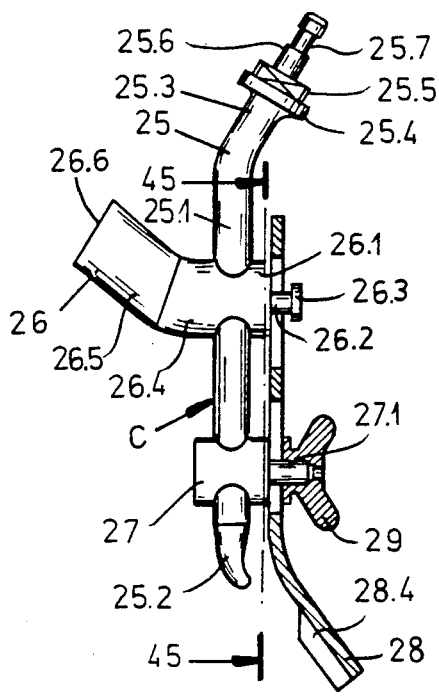 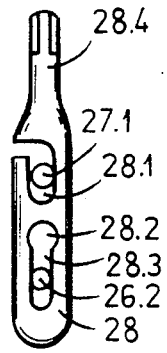 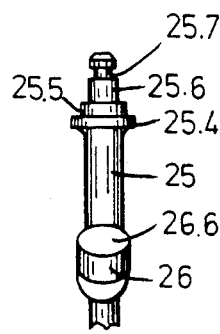
FIG.44  FIG.45  FIG.46
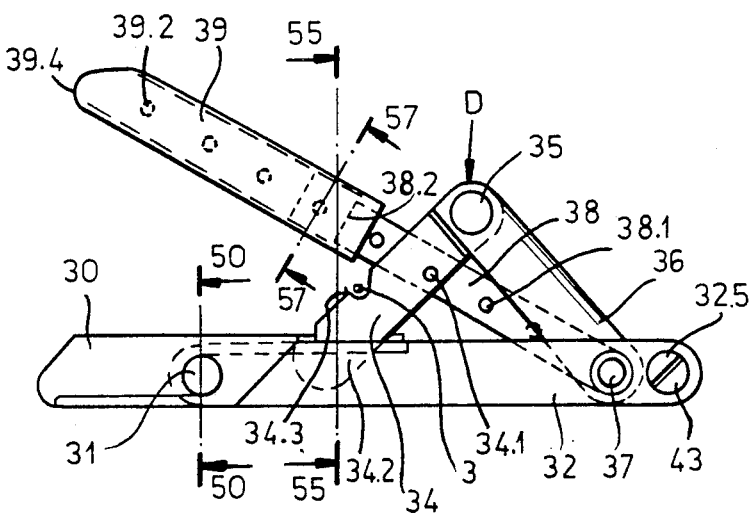
FIG.49
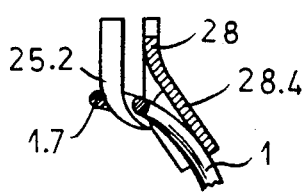 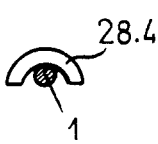 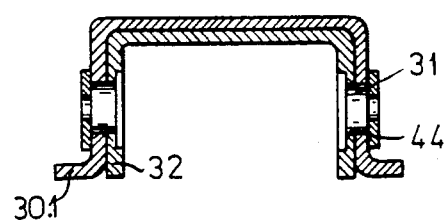
FIG.47  FIG.48  FIG.50

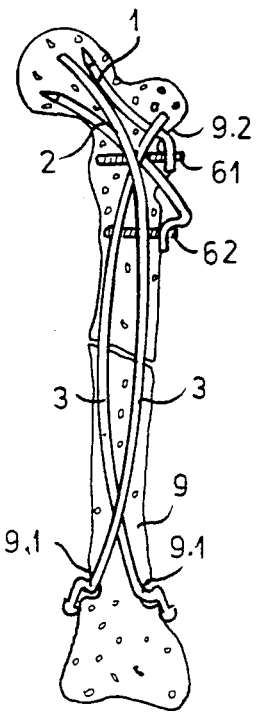 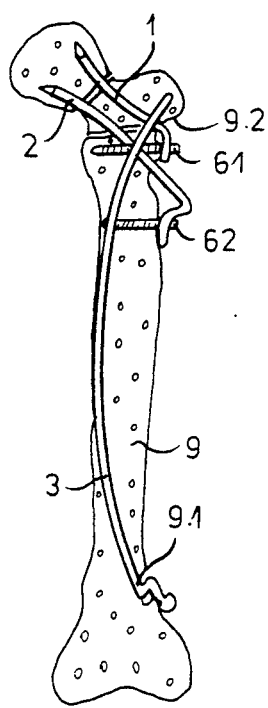 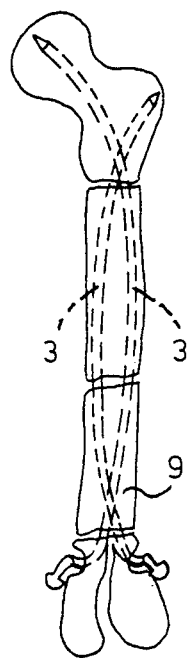 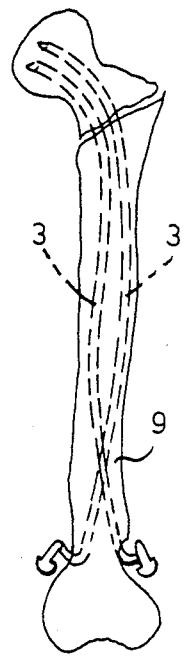
FIG.66  FIG.67  FIG.68  FIG.69
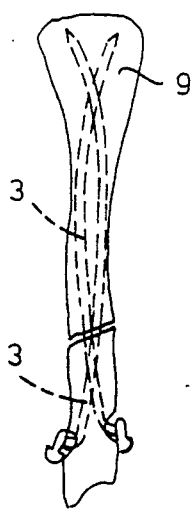 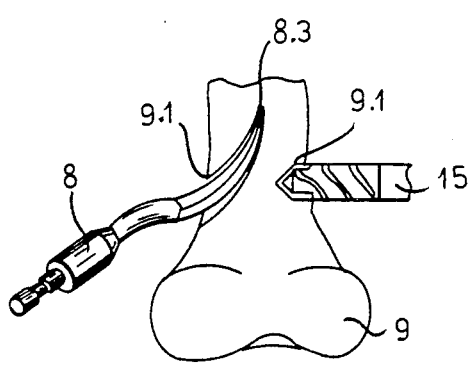 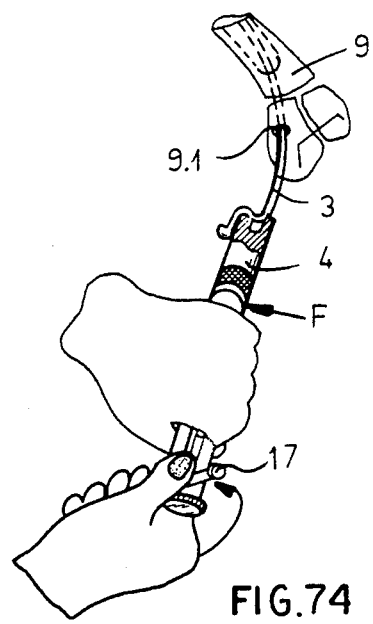
FIG.70  FIG.71  FIG.74

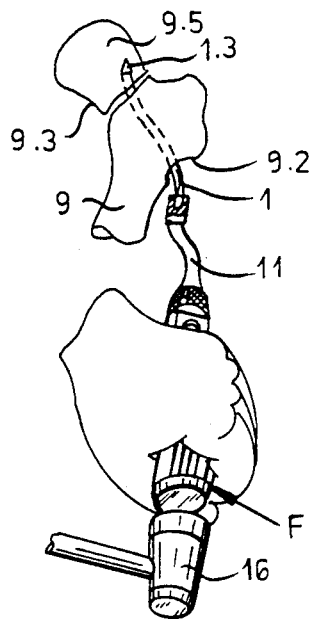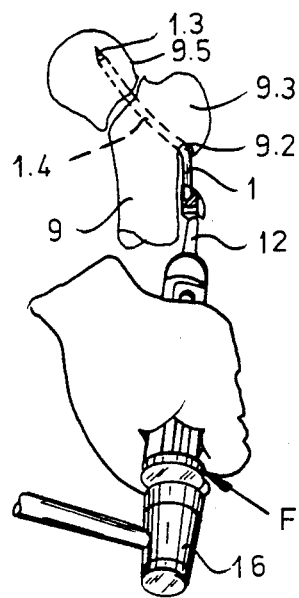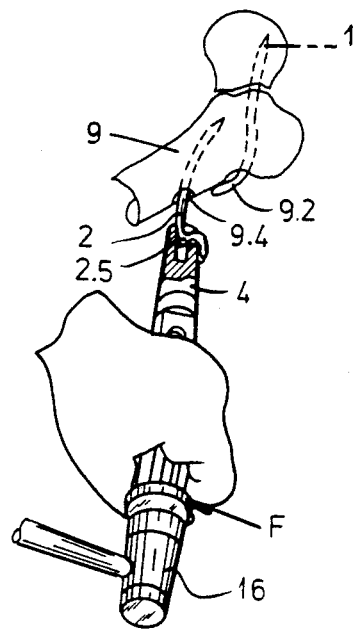
FIG.83  FIG 84  FIG.85
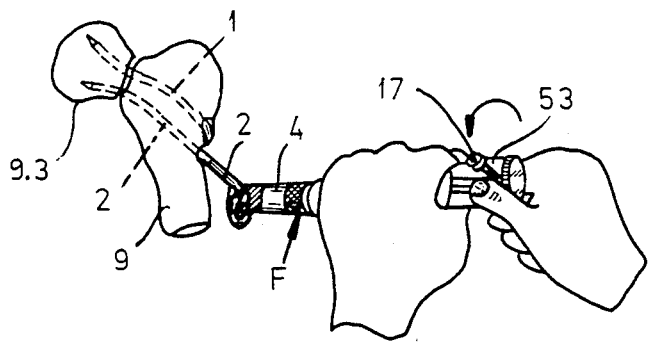
FIG.86
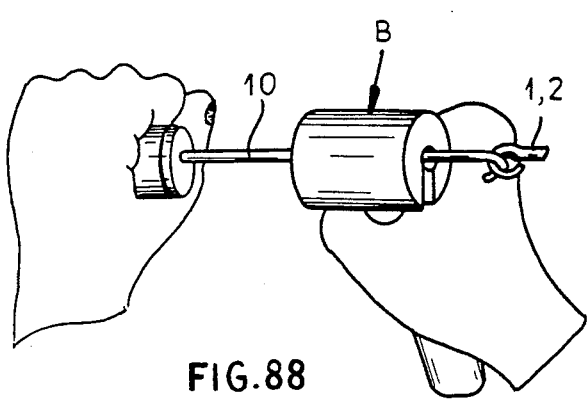
FIG.88
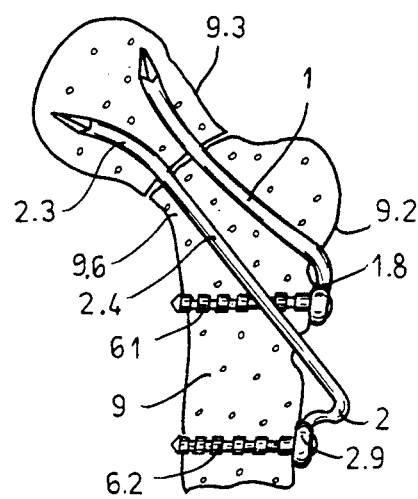
FIG.87

INSTRUMENTATION AND METHOD FOR INSERTING FLEXIBLE IMPLANTS INTO FRACTURED BONES

CROSS-REFERENCE TO RELATED APPLICATION

The present application is a continuation-in-part of copending application Ser. No. 097,968, filed as PCT RO86/00001 on Sep. 18, 1986, now abandoned.

1. Field of the Invention

The present invention relates, in general, to instruments for inserting flexible implants into fractured bones, and, more particularly, to specific tools used to insert specific implants choosen according to the type and location of the fracture, and to the method used for inserting the various implants, as well as the tools used for the extraction of these implants from a mended bone and the method for doing same.

BACKROUND OF THE INVENTION

Long flexible implants for the osteosynthesis of tibia diaphysary fractures and of femur super-intercondylian, mediodiaphysary and subtrochanterian fractures or of unstable fractures of the greater trochanter are already known in the art, and comprise an elongated, thin body formed with a long central portion joined by a curve to a short, forward end, and by another curve to a rear portion which extends to a flattened end formed with a window.

Somewhat shorter flexible implants for the osteosynthesis of femoral neck fractures are also known in the art, and comprise a body formed with a straight, elongated central portion joined through a curve to a short forward end, the central portion extending to a flattened rear portion formed with a window or a projecting finger.

The disadvantages of these known implants lies in the fact that introducing more than two implants is difficult and the mounting finally obtained is highly rigid, which acts to prolong mending of the fracture, the increased mending time in turn acting to increase the possibility of slippage and perforation of the tegument or the medullary channel, which leads to the loss of stabilization of the fracture gap.

Instruments for the introduction into, or extraction from, the bone, are known in the art and in one embodiment, comprise a force-directing tool having a body provided with a forward end formed with a channel adapted to engage the flattened end of a long implant, a hole being provided in a central part of the tool body and adapted to receive a handle for the rotational manipulation of the implant during hammering thereof (French Pat. No. 2,237,609).

An instrument for separating the flattened part of the implant from the diaphysis cortical shell of the bone prior to extraction is known, and comprises a tool having an elongated body provided with a key-shaped forward end adapted to engage the flattened end of the implant (Synthesis catalog). Another instrument for separating the flattened end of the implant from the bone shell is also known, and comprises a tool having a body formed with an upwardly curved flattened end adapted to engage the flattened end of the implant (Prospectus OEC-B76).

An instrument for forming a bore in the bone along a particular pathway for the introduction therein of an implant is known in the art, and comprises a body having a straight portion formed with a forward portion inclined thereto and extending, upwardly curved, with four edges each lying along straight lines converging to a tip (Prospectus OEC-B58).

An instrument for the extraction of a long implant from the bone is known in the art, and comprises a tool having an elongated body formed by a handle provided with a long, rod-like projection adapted to engage the window formed in the flattened part of the implant (AESCULAP catalog, p.42).

An instrument for the force-directing of the shorter implants into the femoral neck is known in the art, and comprises a tool having a crank-shaped body formed with a channel in an active end thereof adapted to engage the flattened end of the implant, and a rod mounted at a central part of the body for positioning the implant during hammering (French Pat. No. 2,237,609).

An instrument for modifying the curvature of an implant is known in the art, and comprises a handle to which a body is attached, the body being provided with two fixed jaws inclined to the body and defining an opening into which the implant is introduced for bending (AESCULAP catalog, p.27).

An instrument for guiding a long implant during hammering is known in the art, and comprises a tool having an elongated, cylindrical body in which the implant is introduced into an opening, the body being formed with a threaded end fastened to the coupling of an anvil, to which a rod is connected for positioning the implant during hammering (French Pat No. 2,237,609).

Another instrument for extracting an implant from the bone is also known, and comprises a handle provided with an elongated rod having a plate-shaped, flattened free end which is upwardly curved and directed rearwardly toward the handle (Prospectus OEC-C2).

An impact instrument for providing the force necessary to the extraction tool for withdrawing an implant from the bone is known in the art, and comprises a cylindrical body having a handle mounted thereon by two bolts, so as to avoid the risk of seizing the body to the rod of the extraction tool during hammering rearwardly along the rod against the handle (OEC-A59).

An instrument for fastening the implant is shown on page 27 of the AESCULAP catalog.

An instrument for providing the hammering impact force for seating an implant is known in the art, and comprises a cylindrical head finished with flat surfaces and provided centrally with an elongated handle formed with a longitudinaly elongated window (AESCULAP catalog, p.27).

An instrument for driving an implant into the bone is known in the art, and comprises a tool having a cylindrical body formed at one end with an anvil, and at the other end with a cylindrical head having a diameter greater than that of the body, the head being formed with a cylindrical channel delimited by a straight wall and adapted to engage the flattened end of an implant, and a multi-functional handle adapted to hold the cylindrical body and formed with a longitudinal channel having its fore part delimited by a shaped wall, the longitudinal channel communicating with a transverse channel in which a yoke-ended lock is disposed under the action of a spring (SYNTHESIS catalog).

Some of the disadvantages of the instrumentation lie in the fact that the instruments or tools for force-directing the long implants into the bone, for separating the flattened implant ends from the bone shell, for force-directing the short implants into the femoral neck, for guiding the long implants, and for driving the implants into the bone, respectively, cannot be used unless the implants are formed with a flattened end or a projecting finger-like end.

The instrument modifying the curvature of the implants does not provide proper fastening of the implants, except into a central portion thereof.

The extraction instrument provided with the rearwardly directed plate-shaped end can only be used with implants provided with the finger-like projections.

The instrument for providing the impact force to the extraction tool required to withdraw an implant from the bone is difficult to use, since the handle is not rotatable relative to the cylindrical body.

The instrument for driving an implant into the bone requires the application of a relatively large effort when impact forces of high value are necessary, since the multi-functional handle does not enable the application thereby of forces of relatively high value to be imparted to the instruments held in the handle. Further, the instrument cannot be positioned except by rotating the handle.

OBJECTS OF THE INVENTION

It is therefore an object of the present invention to provide the improved instrumentation and method for enabling an improved osteosynthesis which will stabilize bone fractures.

It is another object of the invention to provide an improved osteosynthesis which will enable recovery in a short period of time.

It is still another object of the invention to provide an improved osteosynthesis which will enable a less injurious procedure.

It is yet another object of the invention to provide an improved osteosynthesis with minimal blood losses.

It is a further object of the invention to provide an improved osteosynthesis which will minimize the premature and later local and general complications of bone fractures.

SUMMARY OF THE INVENTION

The present invention provides the instrumentation and a method for inserting improved flexible implants into fractured bones, achieving a mounting which stabilizes the fracture gap while providing the benifits of a flexible osteosynthesis, which is known to improve the mending of all fractures of the femur and tibia diaphysis. The stability of the mountings over the course of time is ensured in the case of short flexible implants, used in fractures of the femoral neck, by their fastening to the bone with orthopedic screws, and in the case of long flexible implants, used in fractures of the femur and tibia, by the shape of the lower end, which is seated in the hole made in the bone for the introduction therein of the implant, with the last part of the implant seated on the cortical shell adjacent the hole, the procedure using the short implants or the long implants being easily performed with the instrumentation adapted to the implant shapes and according to the requirements of the procedure time.

According to the present invention, the short implants comprise two types of short rods, one of which is disposed above the other in the osteosynthesis of femoral neck fractures, and the long implants comprise one type of long rod, used singly or in combination with a second long rod and the short rods when stabilizing double gap fractures, those which cross the femur neck and every part of the femur below the greater trochanter, or with one other long rod for stabilizing the diaphysary fractures of the tibia and femur and, respectively, the super- and intercondylian fractures of the femur.

Taken in the upright standing position of the leg, the upper short rod has a straight central portion extending forwardly through a curve to an upwardly inclined pointed end forming an angle with the central portion, which also extends rearwardly through another curve to a downwardly inclined lug end.

The lower short rod has a downwardly curving central portion extending forwardly to a pointed end and rearwardly through an S-curve bending outwardly and inwardly to a lug end.

The long rod is formed by an elongated, straight portion with a pointed upper end, which acts to promote penetration and directing in the bone, the lower part of the straight portion extending through an S-curve bending upwardly and downwardly and extending further through a narrow, flat portion to a widened, flat or arcuate end portion dimensioned so as to prevent the complete penetration of the long rod into the medullary channel of the bone, with the widened end portion resting on the outer cortical shell of the bone.

According to the present invention, the instrumentation comprises tools designed specifically to sucessfully drive the various implants described above into the bone in a manner which will meet all of the objects outlined above.

A tool for the initial introduction and hammering of the long rod and the lower short rod into the bone has a short, straight body with a forward end formed with an elonagted recess having an internal pocket adapted to engage and hold the respective S-curve portions of the long or lower short rods as they are introduced into the bone through a pre-drilled opening. Further, the rear end of the tool is provided with formations enabling the tool to be held in a multi-functional handle.

A tool for the final hammering of the long rod into the bone has an elongated, straight body with a forward end formed with a recess adapted to engage the S-curve portion of the long rod. The rear end of the tool is provided with formations enabling the tool to be held in the multi-functional handle.

After the final hammering of the long rod, another tool is provided for seating the upwardly bending curve of the long rod in the drilled opening of the bone, with the widened end portion resting on the outer bone shell, the tool having an elongated body formed with two inclined flanks tapering forwardly to an arcuate recess adapted to engage the inside of the upwardly bending curve to drive the long rod downwardly in the bone to seat the upwardly bending curve therein, with the inside of the downwardly bending curve engaging the rim of the drilled opening. The arcuate recess is also adapted to be inserted between the widened end portion of the long rod and the bone shell and penetrating to the inside of the downwardly bending curve, thereby unseating the upwardly bending curve prior to extraction of the rod from the bone. The rear end of the tool is provided with formations enabling the tool to be held in the multi-functional handle.

After unseating of the long rod, another tool is provided for lifting the S-curve out of the drilled opening in the bone prior to extraction of the rod from the bone, the tool having an elongated, forwardly tapering body with an upwardly curved leading end, in which there is formed an upwardly facing recess adapted to engage the upwardly bending curve of the rod to lift the curve clear of the opening to enable extraction of the rod. The rear end of the tool is provided with formations enabling the tool to be held in the multi-functional handle.

Once the S-curve of the long rod is clear of the opening, an extraction tool is provided for withdrawing the rod from the bone, the tool having an elongated, thin body tipped with a hook-shaped, rearwardly curved forward end adapted to engage the upwardly bending curve of the long rod or the lug ends of the upper and lower short rods. The rear end of the tool is provided with formations enabling the tool to be held in the multi-functional handle.

A boring tool is provided for forming an arcuate passage from the openings drilled in the flanks of the tibia or femur bones, which arcs into longitundinal alignment with the respective bone for the introduction therein of the long rods to a certain position. The tool has a body formed respectively with a short, straight central portion extending forwardly to a shaped, arcuate portion having cutting edges converging forwardly to a sharp point. The rear end of the tool is provided with formations enabling the tool to be held in the multi-functional handle.

A tool for the initial introduction of the upper short rod into the femur head to an adjustable depth is provided, the tool having an elongated, straight central portion with a forward end disposed at an obtuse angle to the longitudinal axis of the central portion and adapted to engage the lug end of the rod, with the forward end of an axially adjustable plate being formed so as to partially surround the lug end of the rod for guiding the same, and to act as a stop after a predetermined amount of penetration into the bone of the rod. The rear end of the tool is inclined in the same direction as the forward end and is provided with formations enabling the tool to be held in the multi-functional handle. The central portion is further provided with an anvil having an inclined impact portion having a longitudinal axis substantially parallel to that of the forward end.

A force-directing tool is provided for driving the upper short rod into the femur head of the bone in an intermediary stage of the introduction, the tool having a crank-shaped body with a forward end formed with a semi-circular seat adapted to engage the circular lug end of the upper short rod. The rear end of the tool is provided with formations enabling the tool to be held in the multi-functional handle, which is offset from the forward end and acts at an oblique angle thereto and substantially parallel to the the straight central portion of the upper short rod, thereby preventing canting of the rod during hammering.

Another tool is provided for the final seating of the upper short rod in the femur head of the bone, the tool having a short, straight body tipped with a generally spherical head having a flat face forming an obtuse angle with the longitudinal axis of the body, the face being formed with a semi-circular recess having a forwardly directed opening adapted to engage the circular lug end of the upper short rod in a manner which allows the flat face to lie parallel to the surface of the bone and ride therealong, with the lug end of the rod coming to rest on the bone shell. The end of the tool opposite the spherical head is provided with formations enabling the tool to be held in the multi-funtional handle.

A positioning tool is provided for changing the position of the lug ends of the upper and lower short rods after their introduction into the femur head, the tool having an elongated, straight body formed with a cylindrical head in which there is provided a recess opening outwardly at the cylinder wall and adapted to engage the respective lug ends of the upper and lower short rods. The end of the tool opposite the cylindrical head is provided with formations enabling the tool to be held in the multi-functional handle.

Another extraction tool is provided for withdrawing the long rod from the bone by engagement with the widened end part thereof, the tool comprising an elongated body formed with a handle from which there projects a long, thin shaft tipped with a hook-shaped, rearwardly curved, bifurcated claw, adapted to flank the rod and engage the forward facing edges of the widened end part. The handle is provided with an elongated window through which a crossbar or similar device can traverse to aid in the withdrawal of the long rod.

An impact tool is provided for creating the forces which may be necessary to remove the upper and lower short rods and the long rod from the bone using the extraction tools described above having the hook-shaped ends, the tool comprising an elongated handle coupled to a cylindrical head having a longitudinal axis disposed transverse to that of the handle, with an elongated channel formed in the head and centered on the axis thereof, the channel opening sideways through an elongated slit also formed in the head and having a width less than that of the channel and adapted to admit the respective shafts of the extraction tools to the channel, whereby the impact tool can be driven rearwardly against the respective handles of the extraction tools to provide the necessary forces.

Another impact tool is provided for creating the forces which may be necessary to drive the upper and lower short rods and the long rod into the bone, and comprises an impact head having a central section formed as a truncated cone, delimited at the larger end with a large cylindrical section and at the smaller end with a small cylindrical section, and an elongated handle extending from the truncated portion of the impact head at the smaller end thereof, providing a relatively large inertia moment, with the longitudinal axis of the handle lying perpendicular to that of the head.

A rotation tool is provided for altering the penetration direction of the lower short rod and the long rod in the bone by operating the tool as a crank in engagement with the multi-functional handle, the tool being formed by an elongated, cylindrical body having both ends formed with respective cylindrical collars, at least one of which is provided with a recess shaped so as to enable the seating therein of the inwardly bent curve of the lower short rod or the upwardly bent curve of the long rod, providing an alternative mode of rotating the rods.

A tool is provided for guiding the long rods when they are being introduced into the bone by hammering, the tool being formed by an elongated body having a fixed jaw at one end thereof, juxtaposed with an adjustable jaw displaceable on a stud extending from the fixed jaw, both jaws being formed with a respective groove extending across the respective confronting face thereof and adapted to act as a guide for preventing bending of the long rods during hammering. The end of the body opposite the jaws is provided with formations enabling the tool to be held in the multi-functional handle.

The multi-functional handle is provided to interchangeably hold various working tools used for the introduction of the rods into the bone, the handle comprising an elongated, shaped body formed with a longitudinal, elongated window having an enlarged end through which the rotation tool can be introduced and operated as a crank to change the position of the body and any tool held therein about the longitudinal axis of the body. The body is unitary at one end with an anvil to which the impact forces can be applied, and at the other end with a cylindrical, tool gripping head formed with an axially disposed cylindrical channel extending to a recess delimited by a noncircular wall and opening into a cylindrical seat, the channel, the recess and the seat being adapted to engage the formations provided on the various tools. Another cylindrical channel is formed in the head offset from, and transverse to, the longitudinal axis, and intersecting the axially disposed channel tangentially. A shiftable, spring-loaded locking member is disposed in the transverse channel and is adapted to engage and releaseably lock the formations provided on the various tools inserted into the tool head.

For introducing the long rods into the shank of the bone, a circular hole is drilled in the side of the bone at the lower end thereof, followed by the introduction into the drilled hole of the arcuate boring tool, with the point reaching into the medullary channel and forming the line of penetration in a longitudinal direction thereof. Next, the long rod is introduced into the medullary channel through the hole, and using the short-bodied, force-directing tool held in the multi-functional, is hammered by the impact tool with the truncated cone-head to an intermediate position of the rod. Any buckling of the long rod which may occur because of resistance of the bone to the hammering can be prevented by guiding the rod with the guiding tool held in another identical multi-functional handle. If so required, the long rod can be rotated inside the medullary channel by the short-bodied, force-directing tool held in the multi-functional handle, into the window of which the rotation tool is inserted for added leverage.

For the final introduction of the long rod into the bone with the widened end part resting against the external surface of the bone shell, the finishing hammering is made with the long-bodied, force-directing tool in contact with the upwardly bent curve of the rod and carried in the multi-functional handle. For seating this curve in the bone, the tool having forwardly tapering, inclinded flanks and held in the multi-functional handle is used to engage the inside of this curve, whereby the rod can be driven rearwardly or downwardly to seat the curve inside the bone at the drilled opening.

After the fractures have healed, the long rods can be extracted from bone by inserting the forward end of the tool having the forwardly tapering, inclined flanks between the widened end part of the rod and the bone shell, and driving the forward end up to the inside of the downwardly bending curve, at which point the multi-functional handle in which the tool is held can be hammered, thereby loosening the S-curve of the rod from the bone and enabling the elongated tool having the upwardly facing recess to be partially inserted in the drilled hole and engage the upwardly bending curve of the rod and by a tilting motion of this tool, lifting the curve clear of the bone. At this point, the extraction tool with the bifurcated claw is used to engage the widened part of the rod. or if necessary, the extraction tool with the rearwardly directed hook-shaped end is used to engage the upwardly bending curve of the rod, in either case to withdraw the long rod from the bone. The complete extraction of the rod from the bone is made by applying rearwardly-directed impact forces on the handle ends of either of the extraction tools using the impact tool provided with the axial channel in the head.

For the initial introduction of the upper short rod into a femoral head having a fractured femoral neck, a hole is drilled in the bone at the femoral head and the upper short rod, using the tool for inserting a rod to an adjustable depth, is guided into the hole and hammered to the predetermined depth, partially seated in the bone. For further seating in the bone, the lug end of the rod is engaged by the crank-shaped tool held in the multi-functional handle, to which repeated blows are applied by the conical-headed impact tool, driving the rod deeper into the femoral head. For the final seating of the rod across the femoral neck, the crank-shaped tool is replaced by the spherical-headed tool, which can lie flush to the bone while driving the rod.

For the initial introduction of the lower short rod into the femoral head having a fractured femoral neck, another hole is drilled in the bone at the femoral head just below the first hole and the lower short rod, using the short-bodied tool held in the multi-functional handle and engaging the inwardly bending curve of the rod, is guided into the hole and driven into the femoral head and across the femoral neck by repeated blows applied to the handle by the conical-headed impact tool.

The position of the upper and lower short rods in the femoral head is maintained by respective screws traversing the respective lug ends of the rods and threaded into the bone.

To extract the upper and lower short rods from the femoral head, the screws are first removed and the extraction tool with the rearwardly-directed, hook-shaped end is used to engage one of the lugs, while the impact tool with the axial channel formed in the head is fitted onto the stem of the extraction tool and used to impart repeated blows against the handle of the tool in a direction away from the bone, thereby drawing the rod out of the femoral head.

In the introduction of the flexible implants into the bone, the sequence of introduction should be to proceed first with the long rods, inserting one or two of them into the femur to just above the fracture gap, followed by the insertion of the upper and lower short rods into the femoral head, and continuing until all of the rods are completely seated, with the screws anchoring the short rods, and the end piece of the long rod resting on the external surface of the femoral condyle.

BRIEF DESCRIPTION OF THE DRAWING

The above and other objects, features and advantages of the invention will become more readily apparent from the following description, reference being made to the accompanying drawing, in which:

FIG. 12 is a detail view showing the forward end of the tool of FIG. 8 engaging the rod of FIG. 4;

FIG. 13 is a side elevational view, with the forward end in section, of another force-directing tool used with the rod of FIG. 4;

FIG. 14 is a top plan view of the forward end of the tool of FIG. 13;

FIG. 15 is a detail view of the forward end of the tool of FIG. 13 showing the rod of FIG. 4 seated therein;

FIG. 16 is a side elevational view of a seating or loosening tool engageable with the curved end of the rod of FIG. 4;

FIG. 17 is a top plan view of the tool of FIG. 16 with the forward end in section;

FIG. 18 is a side elevational view of a lifting tool engageable with the widened end portion of the rod of FIG. 4;

FIG. 19 is a top plan view of the tool of FIG. 18 with the forward end in section;

FIG. 20 is a side elevational view of a boring tool for forming arcuate passages in the bone;

FIG. 21 is a sectional view taken along line 21—21 of FIG. 20;

FIG. 44 is a side elevational view of a tool for driving the rod of FIG. 1 into the bone to a predetermined depth;

FIG. 45 is a sectional view taken along line 45—45 of FIG. 44;

FIG. 46 is a partial front elevational view of the rearward portion of the tool of FIG. 44;

FIG. 47 is a detail view of the forward end of the tool of FIG. 44 in engagement with the rod of FIG. 1;

FIG. 48 is an end view of FIG. 47;

FIG. 49 is a side elevational view of a bending apparatus in an operational position for modifying the curvature of a flexible implant;

FIG. 50 is a sectional view taken along line 50—50 of FIG. 49;

FIGS. 66-70 illustrate various types of bone fractures and the implant configurations needed to stabilize those fractures;

FIG. 71 is a diagrammatic view of the method for forming openings in the bone for the introduction therein of the long rods of FIG. 4;

FIG. 74 is a diagrammatic view showing correction of the penetration direction of the long rod in the bone by rotation of the rod using the tools of FIGS. 8, 38 and 62;

FIG. 83 is a diagrammatic view of an intermediate stage of introduction into the femoral neck of the upper short rod using the tools of FIGS. 24, 37 and 62;

FIG. 84 is a diagrammatic view of the final introduction into the femoral neck of the upper short rod using the tools of FIGS. 29, 37 and 62;

FIG. 85 is a diagrammatic view of the initial introduction into the femoral head of the lower short rod using the tools of FIGS. 8, 37 and 62;

FIG. 86 is a diagrammatic view of the positioning in the femoral head of the lower short rod using the tools of FIGS. 8, 38 and 62;

FIG. 87 is a sectional view of the femoral head showing the upper and lower short rods seated therein; and FIG. 88 is a diagrammatic view illustrating the extraction from the femoral head of the upper and lower short rods using the tools of FIGS. 22 and 42.

SPECIFIC DESCRIPTION

According to the present invention, the flexible implants are formed by short rods 1 and 2, of which one lies above the other in the normal upright position of the patient, in the stabile flexible osteosynthesis of fractures of the femoral neck, and long rods 3, used in pairs in the stabile flexible osteosynthesis of diaphysary fractures of the tibia, the rods 3 being inserted from the bottom of the tibia and extending to the top in the upright position of the patient, starting from the supermalleolar level on either side of the tibia and forming a spatial superposition at two points in the lower and upper parts of the medullary channel. In the stabile flexible osteosynthesis of the superintercondylian in diaphysary or subtrochanterian fractures of the femur, the rods 3 are introduced into the inner or outer condyle or over the condyle, forming a spatial superposition in the lower and upper parts of the medullary channel. In plain or comminuted, inter or pertrochanterian unstable fractures of the greater trochanter, the two rods 3 are introduced over the inner and outer condyle and are spatially superposed at only one point in the lower part of the medullary channel and lie parallel in the femur neck and head.

For stabilizing fractures with a double gap crossing the femur neck and every femoral part located below the greater trochanter, the osteosynthesis is achieved with both rods 1 and 2, together with one or both rods 3.

Figure 1:
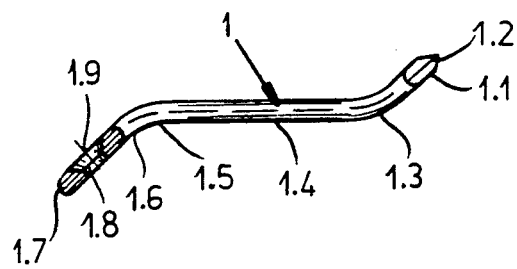
FIG. 1 is a side elevational view of a short implant rod for the osteosynthesis of the femoral neck.
Figure 3:
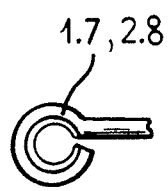
FIG. 3 is a top plan view of the rear ends of the rods shown in FIGS. 1 and 2 which remain in contact with the femoral cortical shell.
Figure 4:
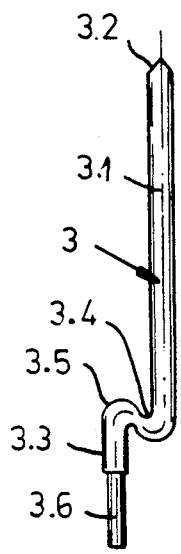
FIG. 4 is a front elevational view of a long implant rod for the osteosynthesis of the femur and tibia.

The rod 1 illustrated in FIG. 1 is formed with a forward portion 1.1 having a shaped end 1.2 which enables the pentration and directing of the rod in the bone 9 when maneuvering from the outside to establish the position required for stabilizing the fracture gap. The forward portion 1.1 is joined by a bend 1.3 to a long, straight portion 1.4 joined through another bend 1.5 having a radius of curvature between 1 and 3 cm and equal to that of bend 1.3, the bend 1.5 being joined to a rear portion 1.6 formed with a lug 1.7. The axis of portion 1.1 is parallel to the axis of portion 1.6 and forms an angle of 40° to 70° with the axis of portion 1.4. The lug 1.7 has a lower flat surface 1.8, delimited by an upper surface 1.9, the cross section of the lug being formed as a truncated cone, with the small base thereof disposed at the surface 1.8.

Figure 2:
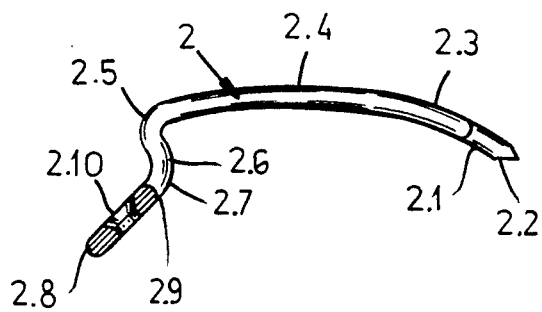
FIG. 2 is a side elevational view of another short implant rod for the osteosynthesis of the femoral neck.
Figure 9:
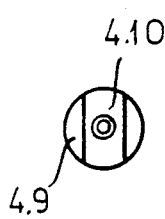
FIG. 9 is a rear end view of the tool of FIG. 8.
Figure 8:
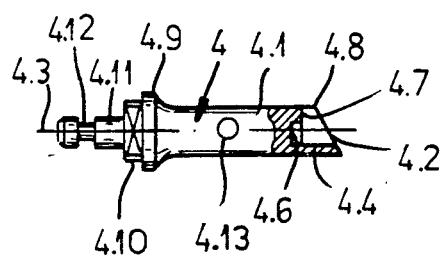
FIG. 8 is a side elevational view, with the forward end in section, of a force-directing tool used with the rods of FIGS. 2 and 4.
Figure 5:
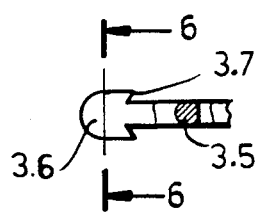
FIG. 5 is a side elevational view of the rear end of the rod shown in FIG. 4 which remains in contact with the femoral cortical shell.
Figure 6:
FIG. 6 is a sectional view taken along line 6—6 of FIG. 5.
Figure 7:
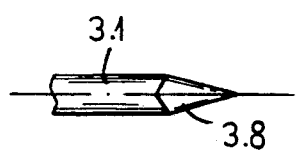
FIG. 7 is a detail view of the forward end of the rod of FIG. 4.
Figure 10:
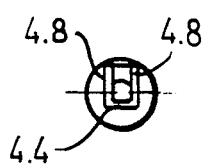
FIG. 10 is a front end view of the tool of FIG. 8.
Figure 11:
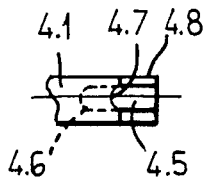
FIG. 11 is a top plan view of the forward end of the tool of FIG. 8.

The rod 2 illustrated in FIG. 2 is formed with a short, straight, forward portion 2.1 having a shaped end 2.2 which enables the penetration and directing of the rod in the bone 9 when maneuvering from the outside to establish the position required for stabilizing the fracture center, and joined by a curved portion 2.3 to a longer curved portion 2.4, which is joined in turn through an S-curve formed with inward and outward bends 2.5 and 2.6 respectively having a radius of curvature less than that of curved portion 2.3, to a rear portion 2.7 formed with a lug 2.8. The latter has a flat lower surface 2.9 delimited by an upper surface 2.10 and having a cross section forming a truncated cone, with the small base thereof disposed at the surface 2.9. The radius of curved portion 2.4 is 7 to 10 cm, while the radius of curved portions 2.5 and 2.6 range between ⅓ to ½ of the radius of curve 2.4. The plane in which the lug 2.8 is disposed forms an angle of 40° to 70° with a horizontal plane, while the axis of portion 2.1 also forms an angle of 40° to 70° to the horizontal plane.

The rods 3, one of which is illustrated in FIGS. 4-7, are formed by a long, normally upright straight portion 3.1 tipped with a pointed forward end 3.2 having flanks with an inclination to the vertical of 30° to 45°, which enables maneuvering of the rod 3 from the outside of the bone 9 to establish the position required for stabilizing the fracture gap. A rear portion 3.3 is joined to the portion 3.1 through an S-curve having inwardly and outwardly curved portions 3.4 and 3.5 respectfully, with curvature radii having values between 3 and 5 cm, and to an end piece 3.6 having a widened, flat or arcuate shape dimensioned so as to stop the complete penetration of a rod 3 into a medullary channel (not illustrated). End piece 3.6 is delimited from part 3.3 by steps 3.7, inclined to the longitudinal axis of rod 3 and forming with it an acute angle of 60° to 75°, symmetrically arranged with the longitudinal axis. Curved portions 3.4 and 3.5 are half flattened and equal to the width of rear portion 3.3 and the diameter of upright, straight portion 3.1 respectfully. The pointed forward end can have edges 3.8 delimiting the faces of the flanks converging on the longitudinal axis of the rod 3.

According to the present invention, the force-directing tool 4 shown in FIGS. 8-12 is used for introducing the rods 2 and 3 into the bone 9, and is formed by a short body 4.1 provided with a forward end 4.2 having a frontal recess 4.3, delimited at the bottom side by a wall 4.4 and defining an elongated seat 4.5 flanked by sidewalls 4.8, the recess 4.3 being provided with a further seat 4.6 formed in a rear vertical wall 4.7 thereof. The shapes of seats 4.5 and 4.6 are selected so as to enable the resting of curve 3.4 in seat 4.6 when the long portion 3.1 of rod 3 extends into the elongated seat 4.5 and curve 3.5 rests in recess 4.3. At the end opposite to the recess 4.3, the body 4.1 has a circular collar 4.9 connected by a noncircular formation 4.10 to a short stub 4.11 formed with a circular seat 4.12. Midway between the ends of the body 4.1, a throughgoing bore 4.13 is formed, having a diameter selected so as to enable the introduction of rod 3 therethrough.

A final force-directing tool 5 is shown in FIGS. 13-15 and is formed by an elongated body 5.1 provided with a forward end having a frontal recess 5.2 delimited at the bottom side by a wall 5.3 and flanked by sidewalls 5.4. A seat 5.5 is formed at the rear of the recess 5.2 and is dimensioned so as to receive the curve 3.4 of rod 3 when introduced therein with the curve contacting the sidewalls 5.4, with the curve 3.5 being positioned externally of the recess 5.2. At the end opposite to the recess 5.2, the body 5.1 has a circular collar 5.6 connected by a noncircular formation 5.7 to a stub 5.8 formed with a circular seat 5.9. Midway between the ends of the body 5.1, a throughgoing bore 5.10 is formed, having a diameter selected so as to enable the introduction of rod 3 therethrough.

Another tool 6 shown in FIGS. 16 and 17 is provided for the final seating of rod 3 in the bone 9, or for the loosening thereof prior to lifting, enabling the extraction of the rod 3 from the bone. The tool 6 is formed by an elongated body 6.1 having two inclined flanks 6.2 with a forward end formed with a frontal recess 6.3, dimensioned so as to enable contact between the body 6.1 and the curve 3.4 of rod 3 without relative movement in a transverse direction between the body 6.1 and the rod 3. A the end opposite to the recess 6.3, the body 6.1 has a circular collar 6.4 connected by a noncircular formation 6.5 to a stub 6.6 formed with a circular seat 6.7 Midway between the ends of the body 6.1, a throughgoing bore 6.8 is formed, having a diameter selected so as to enable the introduction of rod 3 therethrough.

A tool 7 shown in FIGS. 18 and 19 is also provided for lifting the rod 3 prior to extraction thereof from the bone, and is formed by an elongated body 7.1 provided with an upwardly curved leading end 7.2, in which there is formed an upwardly facing recess 7.3 shaped so as to engage the curve 3.4 of rod 3. At the end opposite the recess 7.3, the body 7.1 has a circular collar 7.4 connected by a noncircular formation 7.5 to a stub 7.6 formed with a circular seat 7.7. Midway between the ends of the body 7.1, a throughgoing bore 7.8 is formed, having a diameter selected so as to enable the introduction of rod 3 therethrough.

A boring tool 8 shown in FIGS. 20 and 21 is provided for forming an arcuate passage in the opening 9.1 in the flanks of the tibia or femur bone 9, which arcs into longitudinal alignment therewith for the introduction into the bone of the rod 3 to a particular position. The tool 8 has a body formed respectively by a straight rear portion 8.1 and a shaped, curved forward portion 8.2 tipped with a sharp point 8.3, to which cutting edges 8.4 of portion 8.2 converge, the edges 8.4 being parallel in the first arcuate half a of curved portion 8.2 and converging in the second half a' thereof. The rear portion 8.1 is connected by a circular collar 8.5 connected by a noncircular formation 8.6 to a stub 8.7 formed with a circular seat 8.8.

Figure 22:
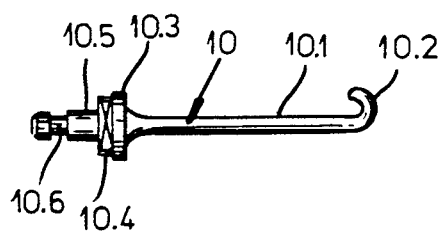
FIG. 22 is a side elevational view of an extracting tool for removing the rods of FIGS. 1, 2 and 4 from the bone.
Figure 23:
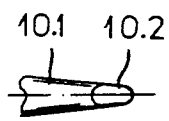
FIG. 23 is a top plan view of the forward end of the tool of FIG. 22.
Figure 25:
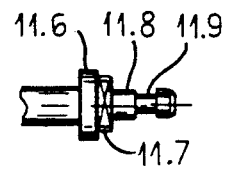
FIG. 25 is a detail view of the rear end of the tool of FIG. 24.
Figure 24:
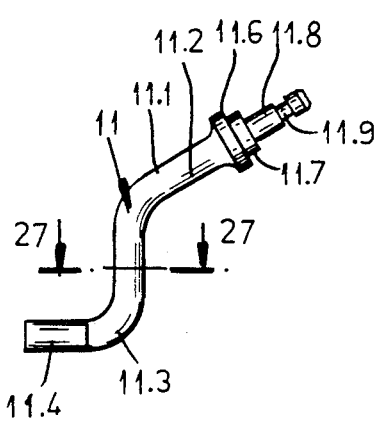
FIG. 24 is a side elevational view of a force-directing tool for driving the rod of FIG. 1 into the bone.
Figures 26, 27:
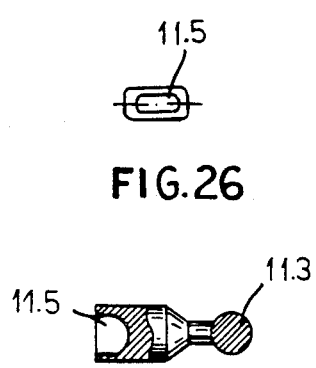
FIG. 26 is an end view of the forward end of the tool of FIG. 24.
FIG. 27 is a sectional view taken along line 27—27 of FIG. 24.
Figure 28:
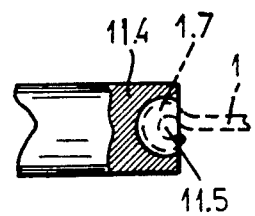
FIG. 28 is a detail view showing the forward end of the tool of FIG. 24 engaging the rod of FIG. 1.

An extracting tool 10 is shown in FIGS. 22 and 23 and is formed by an elongated, thin body 10.1 tipped with a hook-shaped, rearwardly curved forward end 10.2, shaped so as to enable the gripping of curve 3.4 of rod 3, or the rods 1 and 2 by the lug ends thereof. At the end opposite the hook 10.2, the body 10.1 has a circular collar 10.3 connected by a noncircular formation 10.4 to a stub 10.5 formed with a circular seat 10.6.

Another force-directing tool 11 illustrated in FIGS. 24-28 is provided for driving the rod 1 into the bone 9, and is formed by a body 11.1 having various straight portions angled relative to one another and includes a rear portion 11.2 inclined to a normally upright central portion 11.3, which in turn forms a right angle with a forward, flattened portion 11.4, formed with a semi-circular seat 11.5 dimensioned so as to receive the lug 1.7 of rod 1. The rear portion 11.2 has a circular collar 11.6 connected by a noncircular formation 11.7 to a stub 11.8 formed with a circular seat 11.9.

Figure 29:
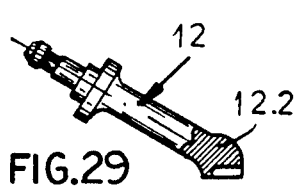
FIG. 29 is a side elevational view, with the forward end in section, of a tool for the final introduction of the rod of FIG. 1 into the bone.
Figure 30:
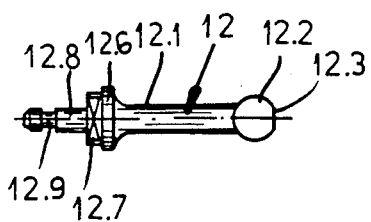
FIG. 30 is a top plan view of the tool of FIG. 29.
Figure 31:
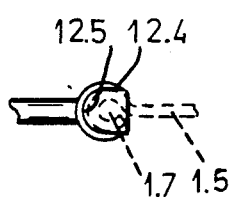
FIG. 31 is a detail view showing the forward end of the tool of FIG. 29 engaging the rod of FIG. 1.

A tool 12 for the final introduction into the bone of rod 1 is illustrated in FIGS. 29-31, and is formed by a short body 12.1 tipped with a generally spherical-shaped forward end 12.2 having a flat frontal face 12.3 formed with a semi-circular recess 12.4 inclined at an angle greater than 90° to the longitudinal axis of body 12.1, the forward end 12.2 having a diameter greater than the rest of the body 12.1. The recess 12.4 is delimited by a semi-circular wall so dimensioned that only the lug 1.7 can be fitted therein, the rest of the rod body being excluded. At the end opposite the recess, the body 12.1 has a circular collar 12.6 connected by a noncircular formation 12.7 to a stub 12.8 formed with a circular seat 12.9.

Figure 32:
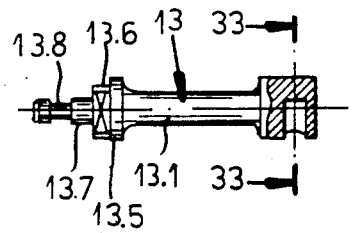
FIG. 32 is a side elevational view, with the forward end in section, of a tool for modifying the position of the rear ends of the rods of FIGS. 1 and 2.
Figure 33:
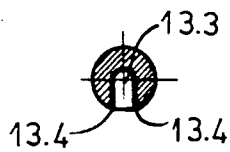
FIG. 33 is a sectional view taken along line 33—33 of FIG. 32.

A positioning tool 13 illustrated in FIGS. 32 and 33 is provided for modifying the position of the ends of rods 1 and 2, and is formed by an elongated body 13.1 tipped with a cylindrical head 13.2 having a diameter greater than that of the body, in which there is formed an outwardly open recess 13.3 adapted to engage the lug ends of rods 1 and 2 and having the longitudinal axis thereof running perpendicular to the axis of body 13.1 and being flanked by flat walls 13.4. At the end opposite to the head 13.2, the body 13.1 has a circular collar 13.5 connected by a noncircular formation 13.6 to a stub 13.7 formed with a circular seat 13.8.

Figure 34:
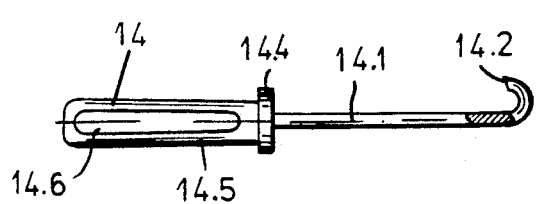
FIG. 34 is a side elevational view of an extraction tool for removing the rod of FIG. 4 from the bone.
Figure 35:
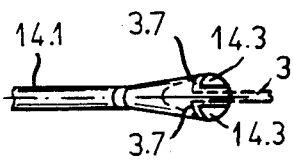
FIG. 35 is a top plan view of the bifurcated forward end of the tool of FIG. 34.

Another tool 14 illustrated in FIGS. 34 and 35 is provided for extracting the rod 3 from the bone 9 by engagement with the the widened end part 3.6 of the rod. The extracting tool 14 is formed by a thin, elongated body 14.1 tipped with a hook-shaped rearwardly curved and widened forward end 14.2, formed by two claws 14.3 shaped so as to enable engagement with the inclined steps 3.7 of rod 3. At the end opposite the claws, the body 14.1 has a circular collar 14.4 joined to a handle 14.5 formed with a longitudinally elongated window 14.6.

Figure 36:
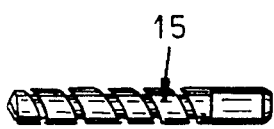
FIG. 36 is a side elevational view of a drill bit for forming the initial opening into the bone.

The drill 15 shown in FIG. 36 is standard in the art and is provided for drilling a hole having a straight axis in the bone 9.

Figure 37:
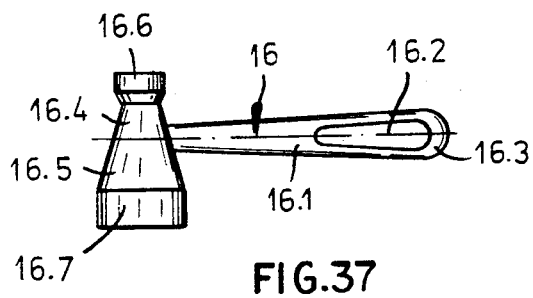
FIG. 37 is a side elevational view of an impact tool for creating the force necessary to drive the rods of FIGS. 1, 2 and 4 into the bone.

An impact tool 16 illustrated in FIG. 37 is provided for creating the impact force necessary for the introduction of rods 1, 2 and 3 into the bone 9, and is provided with a handle 16.1 formed with a longitudinally elongated window 16.2 toward the rear end 16.3 of the handle. The handle 16.1 is unitary with a working head 16.4 having an intermediary section formed as a truncated cone 16.5, delimited respectively by a first cylindrical section 16.6 and a second cylindrical section 16.7, the diameter of the second section 16.7 being greater than that of the first section 16.6. The longitudinal axis of the handle 16.1 is perpendicular to, and intersects, the longitudinal axis of the head 16.4 near the first section, providing a relatively large inertia moment.

Figure 38:
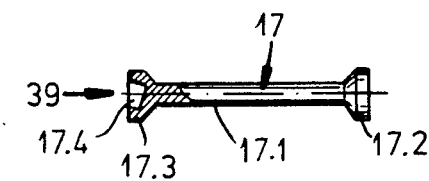
FIG. 38 is a side elevational view, with the forward end in section, of a tool for rotating the rods of FIGS. 2 and 4 in the bone.
Figure 39:
FIG. 39 is an end view taken in the direction of arrow 39 of FIG. 38.

The rotation tool 17 illustrated in FIGS. 38 and 39 is provided for rotating the rods 2 and 3 in the bone 9 by engagement with the multi-functional handle, and is formed by an elongated, cylindrical body 17.1 having a rear end formed with a first circular collar 17.2 and a forward end formed with a second circular collar 17.3 having a diameter less than that of collar 17.2, the second circular collar 17.3 being frontally formed with a circular recess 17.4 shaped so as to enable the seating therein of curved portions 2.5 of rod 2 or 3.4 of rod 3.

Figure 40:
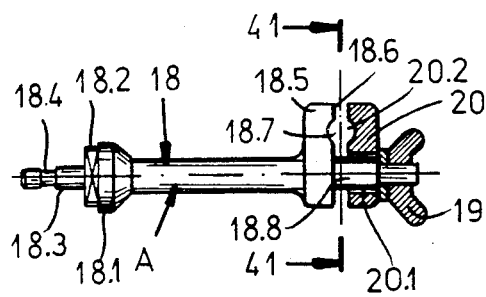
FIG. 40 is a side elevational view, with the forward end in section, of a tool for guiding the rod of FIG. 4 during insertion into the bone.
Figure 41:
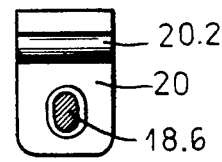
FIG. 41 is a sectional view taken along line 41—41 of FIG. 40.

Another tool A, illustrated in FIGS. 40 and 41, is provided for guiding the rod 3 when it is being introduced into the bone by hammering, and is formed by an elongated body 18 having a saw 18.5 at one end thereof. At the end opposite to the jaw 18.5, the body 18 has a circular collar 18.1 connected by a noncircular formation 18.2 to a stub 18.3 formed with a circular seat 18.4. The saw 18.5 is formed across a frontal surface 18.6 thereof with a semi-circular groove 18.7 having the longitudinal axis thereof perpendicular to that of the body 18. A short, externally threaded stud 18.8 extends from the frontal surface 18.6 centered on the longitudinal axis of body 18 and acts to guide an adjustable jaw 20 fastened thereon by a wing nut 19. The jaw 20 is formed with a bore 20.1 through which the stud 18.8 extends, and semi-circular groove 20.2 extending across the confronting surface of jaw 20 juxtaposed with, and identical to, the groove 18.7.

Figure 42:
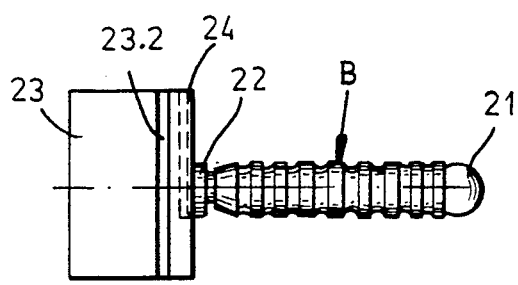
FIG. 42 is a side elevational view of another impact tool for applying the force necessary to the tools of FIGS. 22 and for the extraction of the rods from the bone.
Figure 43:
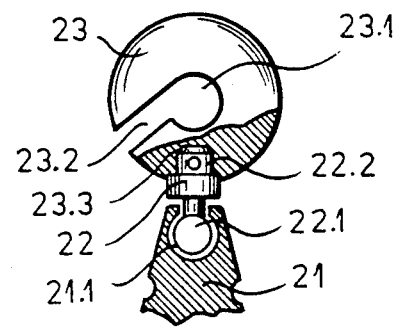
FIG. 43 is a top plan view, partially in section, of the forward end of the tool of FIG. 42.
Figure 51:
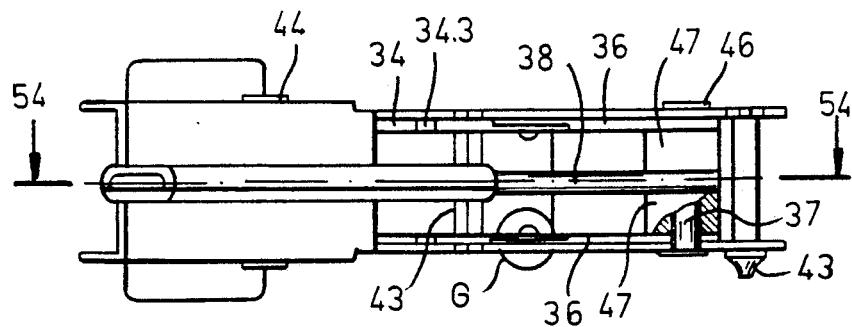
FIG. 51 is a top plan view of the apparatus of FIG. 49.
Figure 52:
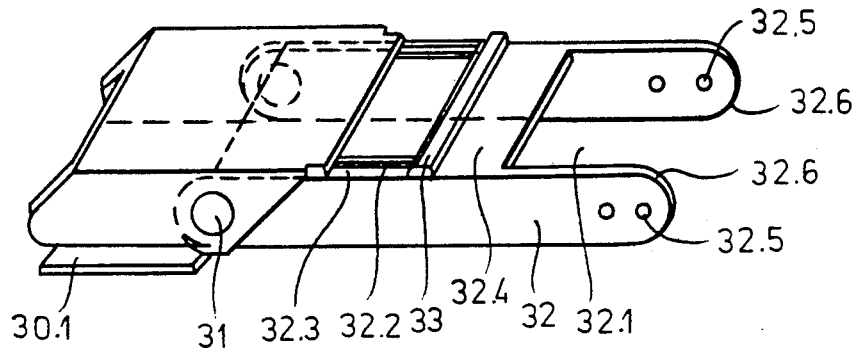
FIG. 52 is a perspective view of the apparatus of FIG. 49 with portions not shown for clarity.
Figure 58:
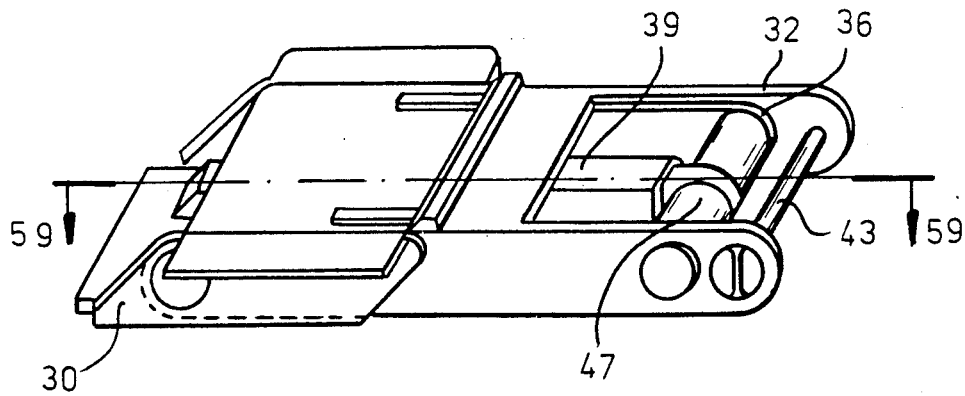
FIG. 58 is a perspective view of the apparatus of FIG. 49 shown in a folded, inoperative position.
Figure 59:
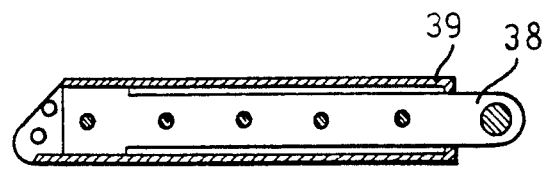
FIG. 59 is a sectional view taken along line 59—59 of FIG. 58.
Figure 54:
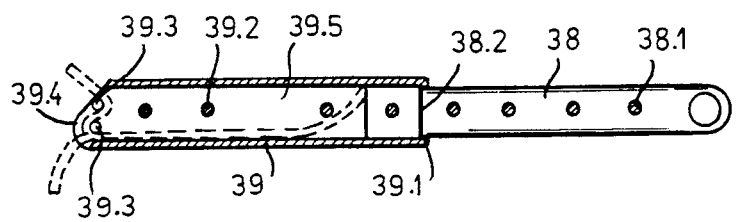
FIG. 54 is a sectional view taken along line 54—54 of FIG. 51.
Figure 55:
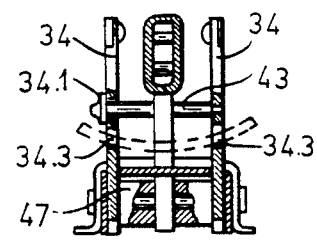
FIG. 55 is a sectional view taken along line 55—55 of FIG. 49.

The tool B shown in FIGS. 42 and 43 provides the impact required for extracting rods 1, 2 and 3 from the bone using the tools 10 and 14, and which comprises an elongated handle 21 coupled through a connecting member 22 with a cylindrical working head 23 having a longitudinal axis lying transverse to the longitudinal axis of handle 21, an elongated channel 23.1 being formed in the head 23 centered on the axis thereof, and opening sideways through an elongated slit 23.2 also formed in the head 23 inclined to the longitudinal axis of handle 21 at an angle of 45°, the width of the slit 23.2 being equal to ½ the diameter of channel 23.1, enabling the introduction of any of the bodies 10.1 and 14.1 of the respective tools 10 and 14. The handle 21 is formed with a spherical recess 21.1 in which a spherical head 22.1 of the member 22 is seated, opposite to which is formed a short, threaded stud 22.2, which is threaded into a threaded bore 23.3 formed in head 23. A pin 24 seated in the head 23 traverses the stud 22.2 for locking the joint together.

A tool C, illustrated in FIGS. 44-48, is provided for introducing the rod 1 into the bone 9 to a depth of 3 to 4 cm, and is formed by a body 25 to which there is fastened an anvil 26 and a support 27. The anvil 26 has a short, cylindrical portion 26.1 provided with a circular stud 26.2 having a head 26.3, and the support 27 has a threaded stud 27.1 which traverses an L-shaped slot 28.1 formed in an elongated plate 28, the slot 28.1 opening at one end thereof at an edge of the plate. A longitudinal slot 28.3 is also formed in the plate 28 and has a circular enlargement at one end thereof of a greater dimension than that of the head 26.3 formed at the end of stud 26.2, enabling the displacement of the anvil along the slot 28.3 when the plate is engaged by the stud 26.2. The plate 28 is adjustably fastened to the support 27 by a wing nut 29 threaded on the stud 27.1. The body 25 has a straight portion 25.1 on which the anvil 26 support 27 are mounted, delimited respectively by a short portion 25.2 inclined to the longitudinal axis of straight portion 25.1, and another portion 25.3 also inclined in the same direction to the axis of portion 25.1. The inclined portion 25.3 has a circular collar 25.4 connected by a noncircular formation 25.5 to a stub 25.6 formed with a circular seat 25.7. The anvil 26 has a straight, upper portion 26.4 joined with an inclined portion 26.5 having the longitudinal axis thereof substantially parallel to that of short portion 25.2, inclined portion 26.5 having a flat end surface 26.6 lying parallel to the longitudinal axis of portion 25.3. The plate 28 is further formed with a shaped end portion 28.4 having an arcuate shape in transverse section, as shown in FIG. 48, and forms an angle with the longitudinal axis of straight portion 25.1 which is 5° to 10° smaller than the angle formed between that axis and the short portion 25.2.

The bending apparatus D, illustrated in FIGS. 49-59, is provided for correcting the curvature of a flexible implant according to the requirements imposed by the location of a fracture in the bone 9. The bending apparatus D comprises a U-shaped sleeve 30 having flared edges 30.1 at the sides and pivotable about short bolts 31 mounted on a U-shaped support 32, at one end of which there is formed a recess 32.1 flanked by a pair of arms 32.6 and separated by a wall 32.4 from a plurality of longitudinal slits 32.2 and 32.3 formed in an upper surface of support 32 at the sides thereof. At an end of the slits 32.2 and 32.3, a stop 33 is provided which coacts with two short arms 34 traversing the slits and pivoted by bolts 35 with two other short arms 36, which are in turn pivotally mounted on flanking arms 32.5 proximal to the free ends thereof by a bolt 37. An elongated, flat arm 38 is also pivotally mounted on bolt 37, and is formed with throughgoing holes 38.1 along the longitudinal axis of the arm. A sleeve 39 is slidably mounted on arm 38 and is formed at one end with a step 39.1 which coacts with a collar 38.2 formed on the arm at the end opposite to the pivot mounting for limiting the displacement of the sleeve 39 therealong. Throughgoing holes 39.2 are formed in the sidewalls 39.5 along the longitudinal axis of sleeve 39 and have the same dimensions and spacing as holes 38.1, with two additional holes 39.3 formed in the sidewall at an inclined end 39.4 opposite to the step 39.1.

Figure 56:
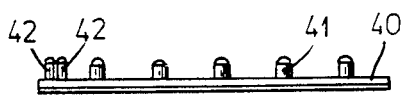
FIG. 56 is a side elevational view of a wall forming a part of the apparatus of FIG. 49.
Figure 57:
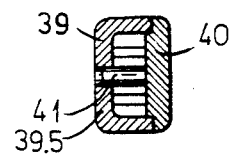
FIG. 57 is a sectional view taken along line 57—57 of FIG. 49.

As can be seen more clearly in FIGS. 56 and 57. the sleeve 39 has a removable sidewall 40 which carries thick pins 41, which can traverse holes 38.1 and 39.2, and a pair of thin pins 42, which traverse holes 39.3. By means of pins 41 and 42, it is possible to position one of the rods 1 and 2 for modifying the curvature thereof depending on the requirements of the bone fracture. For maintaining the arm 38 in the working position shown in FIG. 49, a bolt 43 is introduced into the holes 34.1 formed in the arms 34, the bolt 43 being stored in holes 32.5 of flanking arms 32.6 when not in use. The lower ends 34.2 of the arms 34 are introduced into the slits 32.2 or 32.3, depending on the accentuation of curvature of rod 3 required, the arms 34 being formed with upwardly open recesses 34.3 disposed at the same level when the arms are brought into the working position, in which rod 3 is introduced into the recesses and underlies the arm 38 and sleeve 39. By removing the bolt 43 from the holding position and pivoting the sleeve 39 and arm 38 downwardly, the rod 3 is bent.

For transport or sterilization of the bending apparatus D, the sleeve 39 is displaced along arm 38 and the ends 34.2 of arms 34 are removed from the slits 32.2 and 32.3, which enables the arms 34 and 36 to be folded along with arm 38 and sleeve 39 around bolt 37, so as to lie within within the outline of support 32, a position in which they underlie wall 32.4, and sleeve 30 is folded around bolt 31, locking all of the movable parts in place in support 32.

Figure 53:
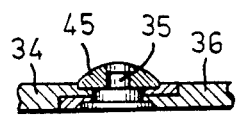
FIG. 53 is a sectional view of detail G of FIG. 51.

The bolts 31, 35 and 37 are secured against loosening by means of nuts 44, 45 and 46, one pair of which is shown in section in FIG. 53. In order to prevent the displacement of the arms 36 and arm 37 during transport, two spacing sleeves 47 are also provided on the bolt 37.

Figure 60:
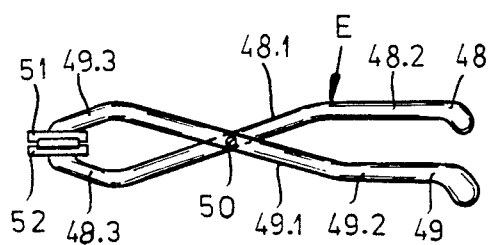
FIG. 60 is a side elevational view of a holding tool.
Figures 62, 63:
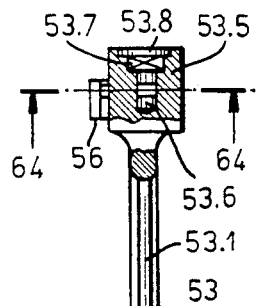
FIG. 62 is a front elevational view of a multi-functional handle.
FIG. 63 is a longitudinal sectional side view of the handle of FIG. 62.
Figure 61:
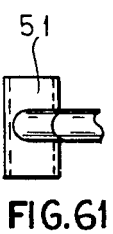
FIG. 61 is a top plan view of the forward end of the tool of FIG. 60.
Figure 64:
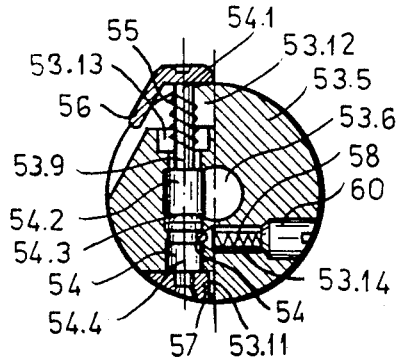
FIG. 64 is a sectional view taken along line 64—64 of FIG. 63.
Figure 65:
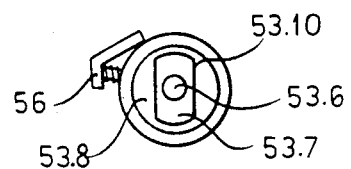
FIG. 65 is a top plan view of the handle of FIG. 62.
Figure 72:
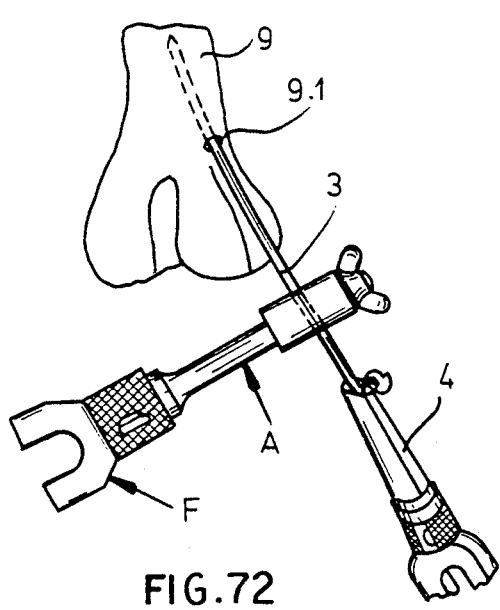
FIG. 72 is a diagrammatic view showing how the long rod of FIG. 4 is prevented from buckling during the initial introduction thereof into the bone by using the guiding tool of FIG. 40.
Figure 73:
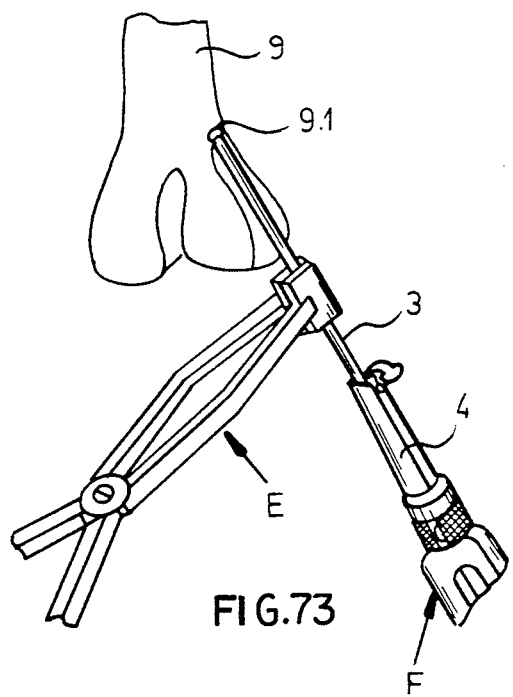
FIG. 73 is a view similar to that of FIG. 72 showing the holding tool of FIG. 60 being used to prevent buckling.

The holding tool E illustrated in FIGS. 60 and 61 is provided for stabilizing the long rods 3 during their initial introduction into the bone, particularly during hammering, and for grasping various instruments for their introduction into, or extraction from, the multi-functional handle F. The holding tool E comprises two arms 48 and 49 pivotally joined by a bolt 50, and formed with intermediary straight sections 48.1 and 49.1 which cross one another and are traversed by the bolt 50. The intermediary sections are inclined to, and unitary with, rear sections 48.2 and 49.2 and front sections 48.3 and 49.3 respectively. The front sections 48.3 and 49.3 are formed with shaped saws 52 and 51 respectively, which are shaped to follow the external shape of rod 3.

The multi-functional handle F illustrated in FIGS. 62-65 is provided to hold the various working tools used for the introduction of the rods into the bone. The handle F comprises an elonagted, shaped body 53 formed with an elongated longitudinal window 53.1 having an enlarged end 53.2, through which the rotation tool 17 can be introduced so as to change the position of the body 53 about the longitudinal axis thereof. The window 53.1 is formed in a central part 53.3 of the body 53, which is unitary at one end with an anvil 53.4 and at the other end with a cylindrical, tool gripping head 53.5. A first cylindrical, longitudinal channel 53.6 is formed in the head 53.5 and extends to a recess 53.7 delimited by a noncircular wall 53.10, the recess 53.7 opening into a cylindrical seat 53.8, shown with particularity in FIGS. 63 and 65. A second cylindrical channel 53.9 is formed in the head 53.5 offset from the first channel 53.6 but intersecting same tangentially and having a longitudinal axis lying perpendicular to that of body 53. At opposit ends, the channel 53.9 opens into respective recesses 53.11 and 53.12, and is provided with a shiftable lock 54 disposed therein and formed at one end as a thin shaft 54.1, with a diameter less than that channel 53.6 and extending into the recess 53.12, and at the other end as a cylinder 54.2 having the same diameter as channel 53.9, the cylindrical portion 54.2 being formed with two circular grooves 54.3 and 54.4, axially shiftable in the channel 53.9. The shaft 54.1 is biased by a spring 55 seated between a shoulder 53.13 of recess 53.12 and a pushbutton 56, formed at the free end of shaft 54.1 and used to axially shift the lock 54 in the channel 53.9 by depressing the pushbutton 56 into the recess 53.12, shifting the cylindrical portion 54.2 clear of the channel 53.6. The end of the cylindrical portion 54.2 opposite the shaft 54.1 is provided with a stop 57, which acts to maintain the lock in the channel 53.9 against the force of the spring 55 with the stop 57 seated in recess 53.11. Another channel 53.14 is formed in the head 53.2 in the same plane as channel 53.9 perpendicular thereto and intersecting same, the channel 53.14 being provided with an indexing ball 59 biased by a spring 58 adjustable by a screw 60, to engage one of the circular grooves 54.3 or 54.4 depending on the position of the circular portion 54.2.

The various types of bone fractures and the implant configurations needed to stabilize those fractures are shown in FIGS. 66-70 and illustrate respectively fractures of the femur and femur neck requiring stabilization by rods 1 and 2 and two rods 3, fractures of the femur neck and the area just below the greater trochanter requiring stabilization by rods 1 and 2 and a single rod 3, fractures of the super and intercondylian, mediodiaphysary and subtrochanterian of the femur requiring stabilization by two rods 3 superposed at two points, a fracture of the greater trochanter requiring stabilization by two rods 3 superposed at only one point, and tibia diaphysary fractures requiring stabilization by two rods 3 spatially superposed at two points.

The method for introducing the various flexible implants into the bone is generally illustrated in FIGS. 66-87.

For introducing the rods 3 into the shank of bone 9, as illustrated in FIGS. 71-74, a circular hole 9.1 is drilled in the bone using the drill 15, followed by the boring tool 8, with the end 8.3 thereof reaching into the longitudinal axis of the medullary channel and forming the line of rod penetration therein. The introduction then of rod 3 into the medullary channel through the hole 9.1 is achieved by use of the force-directing tool 4 held in the handle F. Any buckling of rod 3 which may occur during the introduction because of the resistance of the bone 9 to the blows applied to the handle F by the impact tool 16, can be prevented by guiding the rod 3 with the guiding tool A mounted in a handle F, or with the handling tool E. Depending on the requirements, the rod 3 can also be rotated inside the medullary channel by the tool 4 held in the handle F, into the window 53.1 of which the rotation tool 17 is inserted for added leverage.

Figure 75:
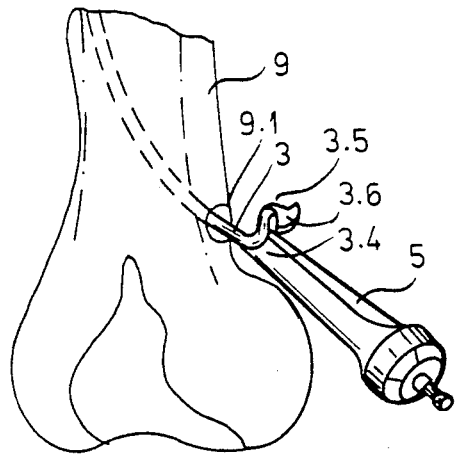
FIG. 75 is a diagrammatic view showing the final hammering of the long rod into the bone using the tool of FIG. 13.
Figure 76:
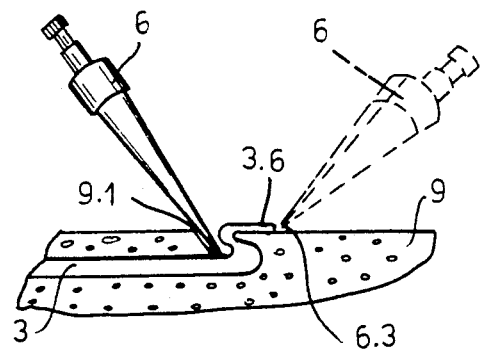
FIG. 76 is a diagrammatic view showing the seating of the long rod in the bone, or the separation therefrom, using the tool of FIG. 16.

For the final introduction of rod 3 into the bone 9 with the end piece 3.6 resting against the external surface of the condyle, as shown in FIGS. 75 and 76, the finishing hammering is made with the force-directing tool 5, carried in handle F, in contact with the curve 3.4. For seating the curve 3.4 in the bone, the tool 6, also held in handle F, is brought to bear on the curve 3.5 to drive the rod 3 slightly rearwardly, or once seated, the end piece 3.6 can be lifted by the tip 6.3 of the tool 6.

Figure 77:
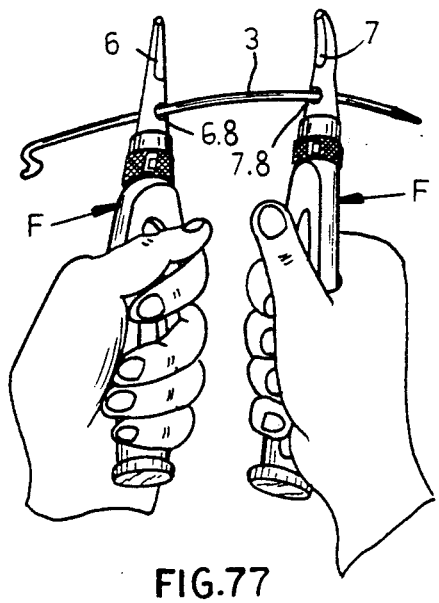
FIG. 77 is a diagrammatic view showing the modification of the curvature of the long rod by using the tools of FIGS. 16, 18 and 62.

Depending upon the requirements, the rod 3 can be manually curved using the tools 6 and 7, in which the rod 3 is introduced through the respective holes 6.8 and 7.8, and the tools 6 and 7 are twisted in opposite directions about their respective longitudinal axes, bending the rod to achieve the curve required (FIG. 77).

Figure 78:
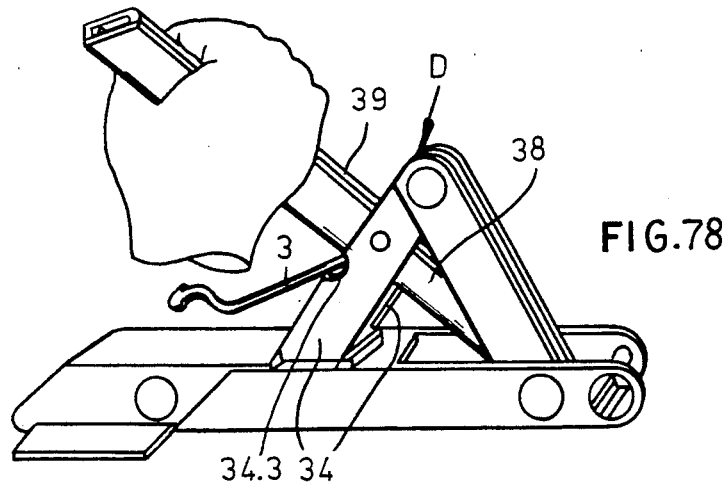
FIG. 78 is a diagrammatic view showing the bending apparatus of FIG. 49 being used for modifying the curvature of the long rod.

The rod 3 can also be curved using the bending tool D, by placing the rod into the recesses 34.3 formed in the arms 34, and pivoting the arm 38 and sleeve 39 downwardly (FIG. 78).

Figure 79:
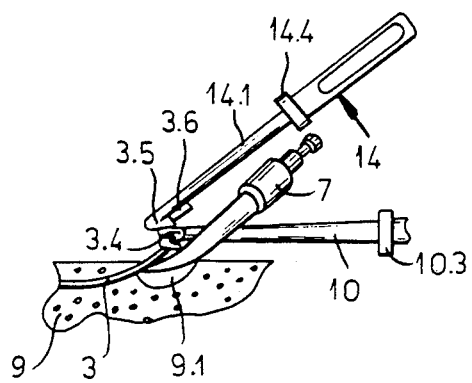
FIG. 79 is a diagrammatic view showing the tools of FIGS. 22 and 34 being used to extract the long rod from the bone.
Figure 80:
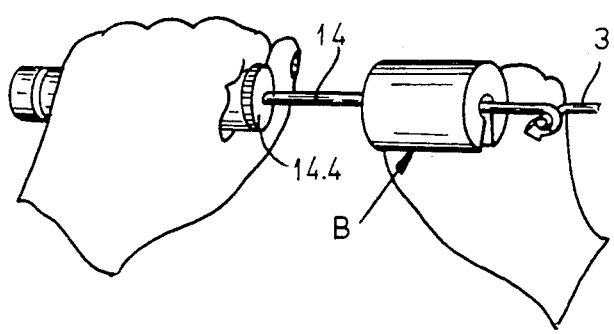
FIG. 80 is a diagrammatic view showing the tools of FIGS. 22 and 42 being used to extract the long rod from the bone.

After the fractures have healed, the rods 3 can be extracted from the medullary channel of the bone 9, as shown in FIGS. 79 and 80, by inserting the frontal recess 6.3 of the tool 6 between the end piece 3.6 of rod 3 and the bone 9 and penetrating up to the curve 3.5, at which point the handle F in which the tool 6 is held can be hammered, thereby loosening the curves 3.4 and 3.4 from the bone and enabling the tool 7 to be partially inserted in the hole 9.1 of bone 9 behind the curves 3.4 and 3.5 of rod 3, and by a tilting motion of the tool 7, lifting the curves clear of the bone. At this point, the tool 14 is used the engage the steps 3.7 of end piece 3.6, and if necessary, the tool 10 is used to engage the curve 3.4, and the rod 3 is drawn. The complete extraction of the rod 3 from the bone 9 is made by applying impact forces on the collars 10.3 and 14.4 of respective tools 10 and 14 by the impact tool B.

Figure 81:
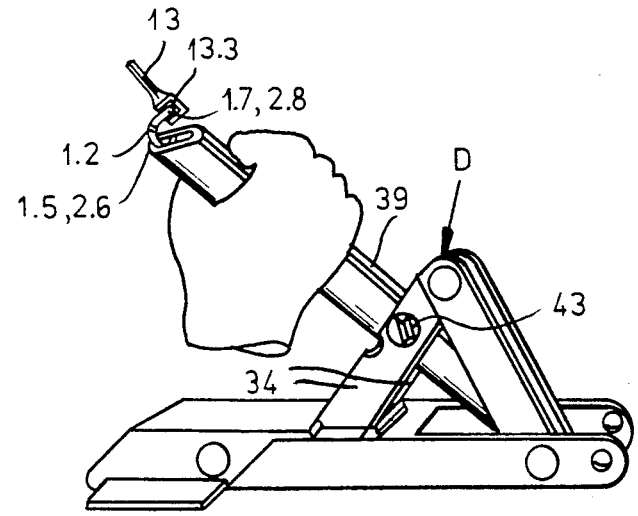
FIG. 81 is a diagrammatic view showing the bending apparatus of FIG. 49 being used for modifying the curvature of the rear ends of the short rods.

In preparation for the introduction of rods 1 and 2 into the bone 9, the curvature of parts 1.5 and 2.6 is modified according to the shape of the bone, by introducing the rods 1 or 2 into the sleeve 39 of bending apparatus D in which they are held fast, and engaging the lugs 1.7 or 2.8 in the seat 13.3 of the tool 13 and bending and twisting to aquire the desired curvature. During the bending operation, the arm 38 on which the sleeve 39 is mounted is fixed to the arms 34 by the bolt 43 to provide the stability necessary during curvature modification (FIG. 81).

Figure 82:
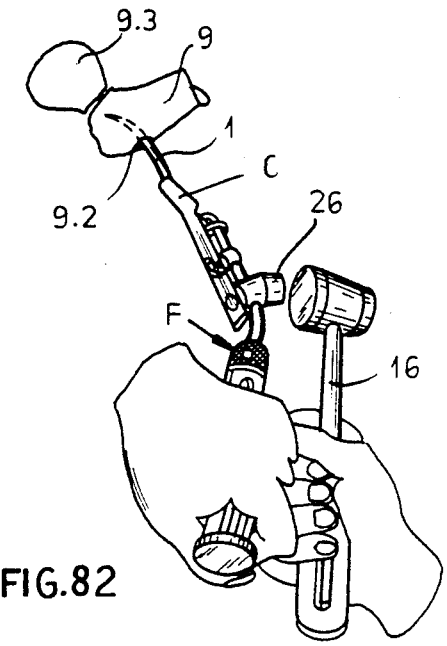
FIG. 82 is a diagrammatic view of the initial introduction into the femoral neck of the upper short rod using the tools of FIGS. 37, 44 and 62.

For the initial introduction of rod 1 into the head 9.3 of the bone 9, as illustrated in FIGS. 82-84, a hole 9.2 is drilled in the bone at the head and the rod 1, held in the tool C, is guided into the hole 9.2 and the anvil 26 of tool C is hammered until the rod is partially seated in the neck 9.3. For further seating in the femur neck 9.3, the lug 1.7 of rod 1 is engaged by the tool 11 held in the handle F, to which repeated blows by the impact tool 16 are applied, driving the forward portion 1.3 of rod 1 toward the superior and external side of the femoral head, whereby the rod is seated near and parallel to the upper edge 9.5 of the femoral neck. For the final seating of rod 1 in the femoral neck 9.3, the tool 11 is replaced with the tool 12, which can lie flush to the bone while driving the rod.

For the initial introduction of the rod 2 into the femoral neck 9.3 of the bone 9, as illustrated in FIGS. 85 and 86, another hole 9.4 is drilled in the bone just below the hole 9.2 and the rod 2, using the tool 4 seated in the handle F and engaging the curve 2.5 of the rod, is guided into the hole and rotated about its longitudinal axis, the tool 17 being engaged in the enlargement 53.2 of handle F to aid rotation, modifying the position of rod 2 in the femoral neck, after which the rod is driven into the femoral neck by repeated blows applied to the handle F. In the final seated position, the rod 2 has the portion 2.4 thereof seated in the lower side of the femoral head near an edge 9.6 of the femoral neck 9.3.

The position of the rods 1 and 2 relative to the bone 9 is maintained by screws 61 and 62 threaded into the bone, whereby the flat surfaces 1.8 and 2.9 respectively of rods 1 and 2 are in direct contact with the cortical shell (FIG. 87).

To extract the rods 1 and 2 from the bone 9, the screws 61 and 62 are first removed and the tool 10 is used to engage one of the lugs 1.7 or 2.8, while the impact tool B is fitted onto the stem 10.1 of the tool 10 and used to impart repeated blows to the collar 10.3 in a direction away from the bone, thereby drawing the rod 1 or 2 out of the bone 9 (FIG. 88).

In the introduction of the flexible implants into the bone, the sequence of introduction should be to proceed first with the rods 3, inserting one or two of them to just above the fracture gap, followed by the insertion of rods 1 and 2 and continuing until all of the rods are completely seated, with the screws 61 and 62 anchoring the rods 1 and 2, and the end piece 3.6 of rod 3 in contact with the external surface of the femoral condyle.

In accordance with the present invention, the implants and the devices or tools used for inserting and extracting them have the following advantages:

the flexible implants, through their structure, enable their use in various groups of two, three and four, in the osteosynthesis of all types of femur fractures and some tibia fractures;

the upper and lower flexible implants used for the osteosynthesis of femoral neck fractures, by their configuration, enables the improved reduction of the fracture through endoosseous taxis, will not damage the intraosseous vascular anastomoses, thereby minimizing the incidence of necroses of the femoral head, enables their fastening by orthopedic screws to the femur diaphysis, providing a mounting with maximum stability over the course of time, the flexible characteristics of the implants with which their divergently curved shapes are associated giving them the ability of acting in a dynamic couple, alternately creating the tensions of traction and compression, which promotes the biologic processes of fracture healing;

when mounted, the long flexible implants which are spatially superposed in the lower and upper parts of the femur or tibia medullary channel, have the lower ends of the implants shaped so as to prevent them from slipping downwardly, thereby avoiding possible perforation of the tegument and local secondary infection therefrom;

when mounted, the long flexible implants which are spatially superposed in the lower part of the medullary channel and parallel in the fermoral neck, stabilize the instabile fractures of the greater trochanter, and the tensions which tend to displace the fracture are taken over through the implants and spread over the two side faces of the lower femur;

the combined use of the short and long implants in double gap fractures of the femoral neck or any other part of the femur preserves the flexibilty of the mounting in the fracture areas and all along the bone line, whereby fast surgical operations are less injurious to the patient;

the tools enable simple and easy maneuvering for the introduction of the implants into, or extraction from, the bone;

the tools have a simple construction and great reliability;

the tools may be easily cleaned and sterilized and do not have areas in which organic remnants from the operation can collect;

the tools can be held in the same multi-functional handle; and the small number of tools having relatively small dimensions ensures achievement of the osteosynthesis of a wide range of fractures.

I claim:

1. An instrument set for driving flexible bone implants into fractured long bones, said set comprising:

a first handle;

a longitudinally elongated window in said first handle;

a first anvil at one end of said first handle;

a tool head at the other end of said first handle for releaseably holding a tool;

a plurality of tools adapted to be held individually and interchangeably in said tool head and including:

a boring tool for forming an arcuate passage from at least one opening drilled in the shank of a bone which arcs into longitudinal alignment with the bone for the initial introduction of a shank implant formed by a long rod, said boring tool having a body formed respectively with a short, straight central portion extending forwardly to a shaped, arcuate portion having a plurality of cutting edges converging forwardly to a sharp point, a rear end of said boring tool being provided with formations enabling said boring tool to be held in said tool head, a first force-directing tool for initially driving the shank implant having a first S-curve adjacent a rear end thereof partially into the bone shank and completely driving a lower femoral head implant formed by a short rod and having a second S-curve adjacent a rear end thereof into the femoral head, said first tool having a short, straight body with a forward end formed with a longitudinally elongated first recess adapted to engage the first and second S-curves of the respective shank and lower femoral head implants, said recess having an internal pocket engageable with a curve of a respective S-curve for supporting the implant, a rear end of said first tool being provided with formations enabling said first tool to be held in said tool head, a second force-directing tool for completely driving the shank implant into the shank, said second tool having a long, straight body with a forward end formed with a longitudinally elongated second recess adapted to engage the first S-curve, a rear end of said second tool being provided with formations enabling said second tool to be held in said tool head, a third force-directing tool for seating the shank implant in the shank, said third tool having an elongated body formed on opposite sides with a respective inclined flank tapering forwardly relative to one another to an arcuate third recess adapted to engage a curve of the first S-curve disposed in the drilled opening for driving the shank implant in a direction opposite to the initial insertion direction for imbedding the curve in the bone tissue surrounding the opening in the shank, a rear end of said third tool being provided with formations enabling said third tool to be held in said tool head, a fourth force-directing tool for initially driving an upper femoral head implant, formed by a short rod and having a circular lug end, partially into the femoral head to an adjustable depth, said fourth tool having an elongated, straight central portion with a forward end disposed at an obtuse angle to the longitudinal axis of the central portion and adapted to engage the lug end of the upper femoral head implant, with a longitudinally adjustable plate mounted on said central portion parallel thereto and having a forward end formed so as to partially surround the lug end of the upper implant for guiding same and to act as a stop after a predetermined amount of penetration of the upper implant into the femoral head, said central portion being further provided with a second anvil having an inclined impact portion with a longitudinal axis substantially parallel to that of said forward end, a rear end of said fourth tool being inclined in the same direction as said forward end and provided with formations enabling said fourth tool to be held in said tool head, a fifth force-directing tool for driving the upper implant partially into the femoral head to an intermediate position, said fifth tool having a crank-shaped body with a forward end formed with a semi-circular first seat adapted to engage the circular lug end of the upper implant, whereby the remaining portion of said crank-shaped body is spaced from the bone, a rear end of said fifth tool being inclined to said forward end and provided with formations enabling said fifth tool to be held in said tool head, a sixth force-directing tool for completely driving the upper implant into the femoral head, said sixth tool having a short, straight body provided with a forward end formed with a generally spherical head having a flat face forming an obtuse angle with a longitudinal axis of said body, said face being formed with a semi-circular fourth recess having a forwardly directed opening, said fourth recess being adapted to engage the circular lug end of said upper femoral head implant in a manner which enables said flat face to ride along the surface of the bone, a rear end of said sixth tool being provided with formations enabling said sixth tool to be held in said tool head, a positioning tool for changing the position of the first lug end of the lower femoral head implant and a second lug end of the lower femoral head implant after their initial introduction into the femoral head of the bone, said positioning tool having an elongated, straight body formed at one end with a cylindrical head in which there is provided a fifth recess opening outwardly at a cylindrical wall thereof and adapted to engage the first lug end or the second lug end, the other end of said body being provided with formations enabling said positioning tool to be held in said tool head, and a guiding tool for stabilizing the shank implants as they are being introduced into the bone by hammering, said guiding tool being formed by an elongated body having a jaw fixed at one end thereof, and an adjustable jaw juxtaposed with said fixed jaw and displaceable relative thereto on a stud extending from said fixed jaw, said fixed jaw and said adjustable jaw each being formed with a respective groove extending across a respective confronting face thereof and adapted to at least in part surround the shank implant for preventing bending thereof during hammering, the end of said body opposite said fixed jaw being provided with formations enabling said guiding tool to be held in said tool head;

a rotation tool for altering the penetration direction of the shank and lower femoral head implants during hammering thereof into the bone, said rotation tool being formed by an elongated, cylindrical body having both ends formed with respective first and second cylindrical collars, said body being adapted to engage said elongated window in said first handle to act as a crank for the rotation thereof, at least one of said first and second cylindrical collars being provided with a sixth recess shaped so as to enable seating therein of a respective curve of the first and second S-curves for providing an alternative means of altering the penetration direction of the shank and lower femoral head implants; and a first impact tool adapted to hammer said first anvil of said first handle for providing the forces necessary to drive said respective shank implant and said lower and upper femoral head implants into said bone, said first impact tool having a first impact head with a central section formed by a truncated cone, delimited at a larger end thereof by a first cylindrical section, and at a smaller end thereof by a second cylindrical section, and an elongated second handle extending from said truncated section of said first impact head adjacent said second cylindrical section and providing a relatively large inertia moment, a longitudinal axis of said second handle lying perpendicular to that of said first impact head.

2. The instrument set defined in claim 1, further comprising:

a lifting tool for engaging and lifting the seated curve of the first S-curve out of the drilled opening prior to extraction of the shank implant from the bone, said lifting tool having an elongated, forwardly tapering body with a curved leading end, a seventh recess being formed on the inside of said curved leading end and adapted to extend into the opening and engage the seated curve of the first S-curve, a rear end of said body being provided with formations enabling said lifting tool to be held in said tool head;

a first extraction tool for withdrawing any of the implants from the bone, said first extraction tool having a first elongated, thin shaft extending from a third circular collar and formed with a first hook-shaped, rearwardly curved forward end adapted to engage either the S-curve of the shank implant or the respective lug ends of the lower and upper femoral head implants, a rear end of said first extraction tool being provided with formations enabling said first extraction tool to be held in said tool head;

a second extraction tool for withdrawing the shank implant from the bone, said second extraction tool having an elongated body formed by a third handle having a fourth circular collar from which there projects a second elongated, thin shaft having a free end formed with a second hook-shaped, rearwardly curved, bifurcated claw, adapted to flank the rod forming the shank implant and engage forward facing edges of a widened end part of the shank implant;

a second impact tool for providing the forces to said first and second extraction tools which may be necessary for withdrawing any of the implants from the bone, said first impact tool having an elongated fourth handle coupled to a cylindrical second impact head having a longitudinal axis disposed transverse to that of said fourth handle, said second impact head formed with a throughgoing, elongated first channel centered on the axis thereof, said first channel also opening sideways through an elongated axial slit formed in said second head and extending between said first channel and an outer cylindrical wall of said second head, said slit having a width less than the diameter of said first channel and adapted to admit said first or second shafts respectively of said first and second extraction tools to said first channel, whereby said respective third or fourth collars can be hammered by said second impact tool in a direction away from the bone.

3. The instrument set defined in claim 2 wherein said toolhead is cylindrical and centered on a longitudinal axis of said first handle, said tool head being formed with an axially disposed cylindrical second channel extending to a noncircular eigth recess opening into a cylindrical second seat, said second channel, said eigth recess, and said second seat being adapted to receive said formations provided on the various tools, with a cylindrical third channel being formed in said tool head offset from, and transverse to, said longitudinal axis and intersecting said second channel tangentially, a shiftable, spring-loaded locking member being disposed in said third channel and adapted to engage and releaseably hold said formations inserted into said tool head, a free end of said locking member extending beyond a cylindrical wall of said tool head and provided with a pushbutton for shifting said member, said cylindrical wall being formed with a ninth recess for accommodating said pushbutton upon depression thereof.

4. An instrument set for extracting flexible bone implants from a mended bone, said set comprising:

a first handle;

an anvil at one end of said first handle;

a tool head at the other end of said first handle for releasably holding a tool;

a plurality of tools adapted to be held individually and interchangeably in said tool head and including:

a force-directing tool for unseating a shank implant from the shank of a femur bone, the shank implant formed by a long rod having a first S-curve adjacent a rear end thereof, the rear end being formed by a substantially flat, widened portion adapted to rest on the outer bone shell when a curve of the first S-curve is seated in an opening drilled in the bone, said force-directing tool having an elongated body formed on opposite sides with a respective inclined flank tapering forwardly relative to one another to an arcuate first recess adapted to be inserted between the widened end portion of the shank implant and the bone shell and penetrating to the first S-curve and engaging same to dislodge the seated curve prior to extraction of the shank implant from the bone, a rear end of said body being provided with formations enabling said force-directing tool to be held in said tool head, a lifting tool for engaging and lifting the unseated curve of the first S-curve out of the drilled opening prior to extraction of the shank implant from the bone, said lifting tool having an elongated, forwardly tapering body with a curved leading end, a second recess being formed on the inside of said curved leading end and adapted to extend into the drilled opening and engage the unseated curve of the first curve, a rear end of said body being provided with formations enabling said lifting tool to be held in said tool head, and a first extraction tool for withdrawing from the bone the shank implant and a lower femoral head implant formed by a short rod having a second S-curve adjacent a rear end thereof, the rear end being formed by a first lug, and an upper femoral head implant formed by a short rod having a second lug at a rear end thereof, said first extraction tool having a first elongated, thin shaft extending from a first circular collar and formed with a first hook-shaped, rearwardly curved forward end adapted to engage either the first S-curve of the shank implant or the respective lug ends of the lower and upper femoral head implants, a rear end of said first tool being provided with formations enabling said first tool to be held in said tool head;

a second extraction tool for withdrawing the shank implant from the bone, said second extraction tool having an elongated body formed by a second handle having a second circular collar from which there projects a second elongated, thin shaft having a free end formed with a second hook-shaped, rearwardly curved, bifurcated claw, adapted to flank the rod forming the shank implant and engage forward facing edges of the widened end part thereof; and an impact tool for providing the forces to said first and second extraction tools which may be necessary for withdrawing any of the implants from the bone, said impact tool having an elongated third handle coupled to a cylindrical impact head having a longitudinal axis disposed transverse to that of said third handle, said impact head formed with a throughgoing, elongated first channel centered on the axis thereof, said first channel also opening sideways through an elongated axial slit formed in said impact head and extending between said first channel and an outer cylindrical wall of said impact head, said slit having a width less than the diameter of said first channel and adapted to admit said first or second shafts respectively of said first and second extraction tools to said first channel, whereby said respective first or second collars can be hammered by said impact tool in a direction away from the bone.

5. The instrument set defined in claim 4 wherein said tool head is cylindrical and centered on a longitudinal axis of said first handle, said tool head being formed with an axially disposed cylindrical second channel extending to a noncircular second recess opening into a cylindrical seat, said second channel, said second recess, and said seat being adapted to receive said formations provided on the various tools, with a cylindrical third channel being formed in said tool head offset from, and transverse to, said longitudinal axis and intersecting said second channel tangentially, a shiftable, spring-loaded locking member being disposed in said third channel and adapted to engage and releaseably hold said formations inserted into said tool head, a free end of said locking member extending beyond a cylindrical wall of said tool head and provided with pushbutton for shifting said member, said cylindrical wall being formed with a third recess for accommodating said pushbutton upon depression thereof.

6. A method of driving a flexible bone implant into fractured long bones, comprising the steps of:
 (a) drilling at least one opening at a lower end of a shank of a long bone;
 (b) forming an arcuate passage in said shank which extends from said opening and arcs into longitudinal alignment with said shank using a boring tool releaseably held in a multi-functional handle;
 (c) introducing a shank implant, formed by a long rod having a pointed front end and an S-curve adjacent a rear end thereof, the rear end being formed by a substantially flat, widened portion, into said passage using a short-bodied, first force-directing tool engaging the S-curve and releaseably held in said multi-functional handle, which is hammered to drive the shank implant to an intermediate position in said shank;
 (d) stabilizing the shank implant during step (c) with a guiding tool acting midway between the ends thereof for preventing bending during hammering, said guiding tool being releaseably held in a second identical multi-functional handle;
 (e) completely driving the shank implant into said shank whereby the widened rear end portion rests on the external bone shell using a long-bodied, second force-directing tool engaging the S-curve and releaseably held in said multi-functional handle which is hammered; and
 (f) seating the shank implant in said shank by engaging a curve of the S-curve disposed in said drilled opening with a third force-directing tool held in said multi-functional handle, which is hammered to drive the curve in a direction opposite to the initial insertion direction of the first implant for imbedding the curve in the bone tissue surrounding said opening.

7. The method defined in claim 6 comprising the further steps of:
 (g) drilling a second opening in a femoral head at an upper end of said shank;
 (h) introducing an upper femoral head implant, formed by a short rod having a lug at a rear end thereof forming an eye, into said second opening using an adjustable, fourth force-directing tool engaging said lug and releaseably held in said multi-functional handle, which is hammered to drive the upper implant partially into said femoral head to a depth determined by said fourth tool;
 (i) driving the upper implant further into said femoral head using a crank-shaped, fifth force-directing tool having a forward end engaging said lug and having a rear end thereof inclined to said forward end and lying substantially parallel to a central portion of the upper implant for directing the driving forces thereto, said rear end being releaseably held in said multi-functional handle, which is hammered to drive the second implant to an intermediate depth in said femoral head;
 (j) completely driving the upper implant into said femoral head using a sixth force-directing tool engaging the lug with a forward end adapted to ride along a surface of the bone, a rear end of said sixth tool being releaseably held in said multi-functional handle which is hammered until the lug is resting against the bone;
 (k) threading a screw into said femoral head through the eye of the upper implant for maintaining the position thereof;

(l) drilling a third opening in the femoral head below the second opening;

(m) introducing a lower femoral head implant, formed by a short rod having a second S-curve adjacent a second lug at a rear end thereof forming an eye, into said second opening using said first tool engaging the second S-curve and releaseably held in said multi-functional handle, which is hammered to drive the lower implant completely into said femoral head with the second lug resting against the bone; and (n) threading a second screw into said femoral head through the eye lower implant for maintaining the position thereof.

8. A method of extracting flexible bone implants from mended long bones, comprising the steps of:

(a) unseating from the shank of a long bone, a shank implant formed by a long rod having a first S-curve adjacent a rear end thereof formed by a substantially flat, widened portion adapted to rest on the outer bone shell when a curve of the S-curve is seated in an opening drilled in the shank, by inserting between the widened end portion and the bone shell, a force-directing tool having an elongated body formed on opposite sides with a respective inclined flank tapering forwardly relative to one another extending to an arcuate first recess, said force-directing tool being held in a multi-functional handle which is hammered to penetrate to the first S-curve and engage same with said first recess to dislodge the seated curve;

(b) lifting the unseated curve of the first S-curve out of said drilled opening using a lifting tool having an elongated, forwardly tapering body with a curved leading end formed with a second recess on the inside thereof and extending into said drilled opening and engaging the unseated curve of the first S-curve, said lifting tool being held in said mulifunctional handle;

(c) withdrawing the shank implant from said shank using a first extraction tool having a first elongated, thin shaft extending from a first circular collar and formed with a first hook-shaped forward end engaging the first S-curve of the shank implant, said first extraction tool being held in said multi-functional handle;

(d) hammering in step (c) in a direction away from the bone, said first circular collar to provide the extra force which may be necessary for withdrawal of the shank implant from said shank using an impact tool having an impact head formed with a throughgoing channel opening sideways through a slit adapted to admit said first shaft to said channel, said impact head being displaced along said first shaft to hammer said first collar;

(e) alternatively withdrawing the shank implant from said shank using a second extraction tool having an elongated body formed by a hanble having a second circular collar from which there projects a second elongated, thin shaft having a free end formed with a second hook-shaped, bifurcated claw flanking the rod forming the shank implant and engaging forward facing edges of the widened end part; and (f) hammering in step (e) in a direction away from the bone, said second circular collar to provide the extra force which may be necessary for withdrawal of the shank implant from said shank using said impact tool as described in step (d).

9. The method defined in claim 8 comprising the further steps of:

(g) withdrawing an upper femoral head implant from a femoral head of said long bone by engaging an eye of the upper implant with said first hook-shaped end of said first extraction tool, the upper implant being formed by a short rod having a lug at a rear end thereof forming said eye;

(h) hammering in step (g) with said impact tool to provide the extra force which may be necessary for withdrawal from the femoral head, as described in step (d);

(i) withdrawing from said femoral head a lower femoral head implant, formed by a short rod having a second S-curve adjacent a second lug at a rear end thereof forming an eye, by engaging either said eye of said second lug or said second S-curve; and (j) hammering in step (i) with said impact tool to provide the extra force which may be necessary for withdrawal from the femoral head, as described in step (d).

* * * * *